United States Patent
Wagner et al.

(10) Patent No.: US 9,174,917 B2
(45) Date of Patent: Nov. 3, 2015

(54) BEXAROTENE ANALOGS

(75) Inventors: Carl E. Wagner, Glendale, AZ (US); Peter W. Jurutka, Scottsdale, AZ (US); Pamela A. Marshall, Glendale, AZ (US); Arjan van der Vaart, Tampa, FL (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 399 days.

(21) Appl. No.: 13/579,551

(22) PCT Filed: Feb. 17, 2011

(86) PCT No.: PCT/US2011/025289
§ 371 (c)(1),
(2), (4) Date: Aug. 16, 2012

(87) PCT Pub. No.: WO2011/103321
PCT Pub. Date: Aug. 25, 2011

(65) Prior Publication Data
US 2012/0309833 A1 Dec. 6, 2012

Related U.S. Application Data

(60) Provisional application No. 61/306,063, filed on Feb. 19, 2010.

(51) Int. Cl.
*A61K 31/03* (2006.01)
*A61K 31/05* (2006.01)
*A61K 31/10* (2006.01)
*C07C 63/66* (2006.01)
*C07C 63/74* (2006.01)

(52) U.S. Cl.
CPC ............... *C07C 63/66* (2013.01); *A61K 31/03* (2013.01); *A61K 31/05* (2013.01); *A61K 31/10* (2013.01); *C07C 63/74* (2013.01)

(58) Field of Classification Search
CPC ........ A61K 31/03; A61K 31/05; A61K 31/10
USPC ........................................................ 514/183
See application file for complete search history.

(56) References Cited

U.S. PATENT DOCUMENTS

| 5,962,731 A * | 10/1999 | Boehm et al. ............... 562/460 |
| 6,162,815 A | 12/2000 | Bernardon |
| 6,258,775 B1 | 7/2001 | Bernardon et al. |
| 6,545,049 B1 | 4/2003 | Canan-Koch et al. |

FOREIGN PATENT DOCUMENTS

| JP | 11-503472 A | 3/1999 |
| WO | WO 94/15902 A1 | 7/1994 |
| WO | WO 2005/000233 A2 | 1/2005 |
| WO | WO 2007/022437 A2 | 2/2007 |
| WO | WO 2011/006157 A2 | 1/2011 |

OTHER PUBLICATIONS

Altucci et al., "RAR and RXR modulation in cancer and metabolic disease", *Nature Rev. Drug Discovery*, vol. 6, 793-810 (2007).
Boehm et al., "Synthesis and Structure-Activity Relationships of Novel Retinoid X Receptor-Selective Retinoids", *J. Med. Chem.*, 37, 2930-2941 (1994).
Boehm et al., "Design and Synthesis of Potent Retinoid X Receptor Selective Ligands That Induce Apoptosis in Leukemia Cells", *J. Med. Chem.*, vol. 38, 3146-3155 (1995).
Daiss et al., "Synthesis, Crystal Structure Analysis, and Pharmacological Characterization of Disila-bexarotene, a Disila-Analogue of the RXR-Selective Retinoid Agonist Bexarotene", *Organometallics*, vol. 24, 3192-3199 (2005).
Dawson et al., "Conformational effects on retinoid receptor selectivity. 2. Effects of retinoid bridging group on retinoid X receptor activity and selectivity", *J. Med. Chem.*, vol. 38, 3368-3383 (1995).
Dawson et al., "The receptor-DNA determines the retinoid response: a mechanism for the diversification of the ligand signal", *Molecular and Cellular Biology*, vol. 16 (8), 4137-4146 (1996).
Dimick et al., "On the Meaning of Affinity: Cluster Glycoside Effects and Concanavalin A", *J. Am. Chem. Soc.*, 121, 10286-10296 (1999).
Faul et al., "Synthesis of Novel Retinoid X Receptor-Selective Retinoids", *J. Org. Chem.*, vol. 66, 5772-5782 (2001).
Fujii et al., "Metabolic inactivation of retinoic acid by a novel P450 differentially expressed in developing mouse embryos", *The EMBO Journal*, vol. 16 (14), 4163-4173 (1997).
Gandi, "Reactions of Some Aromatic Nitro Compounds with Alkali Metal Amides", *J. Org. Chem.*, 44 (25), 4705-4707 (1979).
Gernert et al., "Design and Synthesis of Fluorinated RXR Modulators", *Bioorg. Med. Chem. Lett.*, vol. 13, 3191-3195 (2003).
Heller et al., "Synthetic retinoids in dermatology", *Canadian Medical Association Journal*, vol. 132 (10), 1129-1136 (1985).
Jong et al., "Conformational effects on retinoid recepetor selectivity. 1. Effect of 9-double bond geometry on retinoid X receptor activity", *J. Med. Chem.*, vol. 36, 2605-2613 (1993).
Keenan et al., "Conformational Preferences in a Benzodiazepine Series of Potent Nonpeptide Fibrinogen Receptor Antagonists", *J. Med. Chem.*, 42, 545-559 (1999).
Lehmann et al., "Retinoids selective for retinoid X receptor pathways", *Science*, vol. 258, 1944-1946 (1992).
Michellys et al., "Novel (2E, 4E, 6Z)-7-(2-Alkoxy-3,5-dialkylbenzene)-3-methylocta-2, 4, 6,-trienoic Acid Retinoid X Receptor Modulators are Active in Models of Type 2 Diabetes", *J. Med. Chem.*, vol. 46, 2683-2696 (2003).
Michellys et al., "Design and Synthesis of Novel RXR-Selective Modulators with Improved Pharmacological Profile", *Biorg. Med. Chem. Lett.*, 13, 4070-4075 (2003).
Michellys et al., "Design, Synthesis and Structure-Activity Relationship Studies of Novel 6,7-Locked-[7-(2-alkoxy-3,5-dialkylbenzene)-3-methylocta]-2,4,6-trienoic Acids", *J. Med. Chem.*, vol. 46, 4087-4103 (2003).
Michellys et al., "Design, synthesis and structure-activity relationship of novel RXR-selective modulators", *Bioorg. Med. Chem. Lett.*, vol. 14, 1593-1598 (2004).
Nahoum et al., "Modulators of the structural dynamics of the retinoid X receptor to reveal receptor function", *Proc. Natl. Acad. Sci.*, vol. 104, 17323-17328 (2007).

(Continued)

*Primary Examiner* — Yong Chong
(74) *Attorney, Agent, or Firm* — Viksnins Harris & Padys PLLP

(57) ABSTRACT

The present invention relates to analogs of bexarotene and methods of use thereof.

10 Claims, 3 Drawing Sheets

(56) References Cited

OTHER PUBLICATIONS

Parry et al., "A Boronated Benzamide as Melanoma-Seeking Agent", *Biorg. Med. Chem. Lett.*, 7(3), 361-364 (1997).

Patent Cooperation Treaty, International Searching Authority, Search Report and Written Opinion for PCT/US2011/25289, 8 pages, May 17, 2011.

Prince et al., "Bexarotene capsules and gel for previously treated patients with cutaneous T-cell lymphoma: Results of the Australian patients treated on phase II trials", *Australasian Journal of Dermatology*, vol. 42, 91-97 (2001).

Sakaki et al., "Synthesis and Structure-activity Relationship of Nocel RXR antagonists: orally active antidiabetic and antiobesity agents", *Bioorg. Med. Chem. Lett.*, 17, 4804-4807 (2007).

Shibakura et al., "Anticoagulant Effects of Synthetic Retinoids Mediated Via Different Receptors on Human Leukemia and Umbilical Vein Endothelial Cells", *Blood*, vol. 90, 1545-1551 (1997).

Sporn, "Retinoids and Cancer Prevention", *Cancer Journal for Clinicians*, vol. 29 (2), 120-125 (1979).

Takahasi et al., "2,5-Diaryl-1,3,2-dioxaborinanes: A New Series of Liquid Crystals", *Bull. Chem. Soc.*, 62 (12), 3896-3901 (1989).

Thomas, "Retinoid Metabolism: a balancing act", *Nature Genetics*, vol. 31, 7-8 (2002).

Traynelis, "Ylide Methylation of Aromatic Nitro Compounds", *J. Org. Chem.*, 1966, vol. 31, 243-247 (1966).

Vahlquist, "What are Natural Retinoids?" *Dermatology*, vol. 199, 3-11 (Suppl 1) (1999).

Wagner et al., "Modeling, synthesis and biological evaluation of potential retinoid X receptor (RXR) selective agonists: novel analogues of 4-[1-(3,5,5,8,8-pentamethyl-5,6,7,8-tetrahydro-2-naphthyl)ethynyl]benzoic acid(bexarotene)", *J. Med. Chem.*, 52, 5950-5966 (2009).

White et al., "Identification of the retinoic acid-inducible all-trans-retinoic acid 4-hydroxylase", *Journal of Biological Chemistry*, vol. 271, 29922-29927 (1996).

Zimmerman, "Procedures used in the induction of mitotic recombination and mutation in the yeast *Saccharomyeces cerevisiae*", *Mutat. Res.* 31, 71-86 (1975).

Zimmerman, "A yeast strain for simultaneous detection of mitotic crossing over, mitotic gene conversion, and reverse mutation", *Mutat. Res.*, 28, 381-388 (1975).

Winum et al., "Synthesis of New Targretin® Analogues that Induce Apoptosis in Leukemia HL-60 Cells", *Bioorganic & Medicinal Chemistry Letters 12*, 3529-3532 (2002).

* cited by examiner

BEXAROTENE ANALOGS

RELATED APPLICATIONS

This application is a U.S. 371 application of PCT/US2011/025289, which was filed on 17 Feb. 2011, and claims the benefit of priority of U.S. Ser. No. 61/306,063, filed Feb. 19, 2010, the entirety of which are incorporated herein by reference.

STATEMENT OF GOVERNMENT SUPPORT

This invention was made with government support under CA139364 awarded by the National Institute of Health. The government has certain rights in the invention.

FIELD OF THE INVENTION

The invention relates to new compounds that are bexarotene analogs, compositions comprising the same and methods of use of such compositions.

BACKGROUND OF THE INVENTION

There are two types of retinoids, those that are naturally produced in all living organisms and those known as synthetic retinoids. Natural retinoids are found in all living organisms either as Vitamin A or carotenoids (6). These two types of retinoids are essential for numerous biological processes such as vision, cellular growth and differentiation, and reproduction (6). Synthetic retinoids like isotretinoin, etretinate, and bexarotene are all used to treat people with certain types of skin diseases (3).

Natural retinoids such as retinol (Vitamin A) are synthesized into retinaldehyde and then to all-trans retinoic acid via two oxidation steps (2, 7). The first oxidation step involves the synthesis of retinol to retinaldehyde by means of alcohol dehydrogenase and short-chain dehydrogenase enzymes. The second step involves retinaldehyde to all-trans retinoic acid via three retinaldehyde dehydrogenase enzymes (2, 7). These all-trans retinoic acid is converted to hydroxylated metabolites by cytochrome P 450 enzyme (Cyp 26). This metabolite is critical in developing mice embryos since it protects tissues from inappropriate exposure to all-trans retinoic acid (2, 7).

Synthetic retinoids are derived from retinol (Vitamin A) (4). Although there are several kinds of synthetic retinoids, each was made to perform specific functions in the body (4). Synthetic retinoids were produced to mimic the actions of certain natural retinoids. This was done because the natural retinoids either had severe side effects or different transport mechanisms. For example, when large amounts of natural retinoids are ingested during a meal, it can be highly toxic (4).

The mechanism for natural and synthetic retinoids involves two types of nuclear retinoid receptors; the retinoic acid (RA) receptor and the retinoid X receptor. Both receptors are coded for by three genes (α, β, and γ) from which multiple receptor isoforms can be produced (1). RARs bind and are activated by tRA and 9-cis-RA, whereas RXRs only interact with 9-cis-RA. These receptors mediate retinoid signals by binding to specific DNA sequences or RA responsive elements as RAR-RXR heterodimers or homodimers or by interacting with other transcriptional factors (1). Not only are the RXRs critical for allowing effective binding of the RARs to DNA but it also increases DNA binding to other receptors that work together with different hormones or vitamin derivatives. Thus the RXRs play a vital role in mediating a variety of hormonal signals in the nucleus (1).

Bexarotene (Targretin®) is a pharmaceutical drug used to treat cutaneous T-cell lymphoma as well as off label to treat other types of cancer. Bexarotene is a synthetic retinoid analog with specific affinity for retinoid X receptors (6). Bexarotene is currently an FDA approved drug, effective in the treatment of cutaneous T-cell lymphoma (CTCL), and it is being explored for treatment of breast cancer, lung cancer, colon cancer, and other diseases of uncontrolled cellular proliferation, because activation of RXR and "up-regulation" (or expression) of the genes regulated by RXR seems to have a therapeutic effect by slowing or arresting cellular proliferation in these conditions. Bexarotene and one of its analogs have also been explored as possible treatments for noninsulin-dependent diabetes mellitus (NIDDM) in mouse models. Despite bexarotene's specific activation of RXR, versus RAR, three drawbacks to the use of bexarotene include hypothyroidism, since there may be an unintentional antagonism of the TR receptor with ligand activated RXR39, hyperlipidemia, and cutaneous toxicity as a possible result of residual RAR agonism at the dose concentration. There is also evidence that bexarotene regulates the expression of pyruvate dehydrogenase kinase (PDK4) in the heart. Thus, there is a need to prepare analogues of bexarotene that are specific only for the RXR homodimer such that the therapeutic effects of the bexarotene of inhibiting cell proliferation and treatment of various cancers can be realized without the concomitant detrimental effects of hypothyroidism.

BRIEF SUMMARY OF THE INVENTION

The invention relates to new bexarotene analogs, methods of preparing the same and methods of use of the same in therapeutic embodiments. The analogs have structural features chosen to optimize the RXR agonist properties of the analogs but with lowered toxicity profiles as compared to analogs previously reported.

Particularly preferred analogs of the invention have a structure:

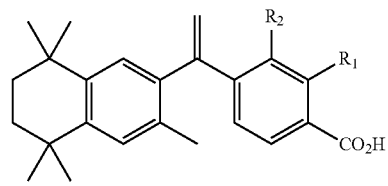

in which substituents at each of positions R1, and R2 are:

| Compound # | R1 | R2 |
|---|---|---|
| 8 | H | F |
| 9 | F | H |
| 10 | Cl | H |
| 11 | Br | H |
| 12 | I | H |
| 10a | H | Cl |
| 11a | H | Br |
| 12a | H | I |
| 10b | Cl | Cl |
| 11b | Br | Br |
| 12b | I | I |

More specifically, a preferred example of the analogs of the invention is a compound of Formula 2 in which R1 is F and R2 is H, i.e., Compound 9 in the table above.

DETAILED DESCRIPTION OF THE INVENTION

Figure 1:
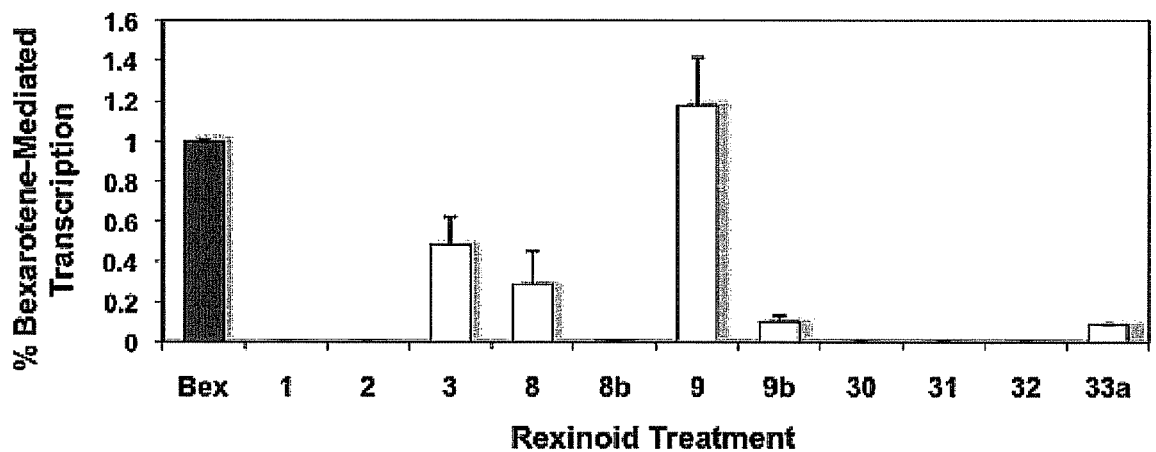
FIG. 1: Identification of potential RXR agonists via a mammalian two-hybrid screening assay in human colon cancer cells.

In the present application there are provided a variety of bexarotene analogues that inhibit cell proliferation. Described herein are methods and compositions for making such analogues and uses thereof in therapeutic compositions.

Bexarotene, commercially known as Targretin®, is a chemotherapeutic indicated for the treatment of cutaneous T-cell lymphoma (CTCL). It is most often prescribed to patients who have been resistant to at least one prior systemic therapy. Bexarotene works by binding with high affinity to the nuclear retinoid X receptor and inducing homodimerization. However, since bexarotene binds specifically to RXR, and RXR is required as a heterodimeric partner for other nuclear receptors (i.e., RAR, VDR, TR), one contraindication for Targretin is its potential to dysregulate these other RXR requiring pathways. More specifically, when bexarotene enters the nucleus of the target cell it recognizes and binds to all retinoid X receptors, including those active in heterodimerization. Thus, when bexarotene binds to RXR as part of a heterodimer, it can cause the heterodimer to dissociate and result in the loss of function of the primary receptor, leading to detrimental side effects in patients treated with this medication.

In the present invention, there are described a variety of bexarotene analogs that have the core structure essential for the compound's ability to bind effectively to RXR. Certain of the exemplary compounds synthesized herein have the formula:

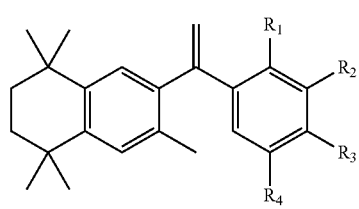

(FORMULA 1)

In the above formula, any of $R_1$-$R_4$ are independently selected from hydrogen, $C_{1\text{-}6alkyl}$, hydroxy, C1-6alkoxy, thiol, halogen, $C(R^6)3$, $CO_2H$, $CO_2C_{1\text{-}6alkyl}$, $SO_3H$, $NH_2$, $NHC_{1\text{-}6alkyl}$ or $N(C_{1\text{-}6alkyl})_2$, provided that at least one of $R_1$-$R_4$ is $CO_2H$. By halogen, it is meant Fl, Br, Cl or I. Where there is more than one halogen moiety at positions $R_1$-$R_4$ the halogens moieties may all be the same or may be different. Specific examples of the compounds of formula 1 are a compound of FORMULA 1 having the following substituents at each of positions R1, R2, R3, R4:

| Compound # | R1 | R2 | R3 | R4 |
|---|---|---|---|---|
| 1 | H | H | H | $CO_2H$ |
| 2 | $CO_2H$ | H | H | $CO_2H$ |
| 3 | H | $NO_2$ | $CO_2H$ | H |
| 4 | H | $CO_2H$ | $CO_2H$ | H |
| 5 | H | $CO_2H$ | $CO_2H$ | $CO_2H$ |
| 6 | F | F | $CO_2H$ | H |
| 7 | H | F | $CO_2H$ | F |

In still other embodiments, a preferred compound of the invention has the general formula of FORMULA 2:

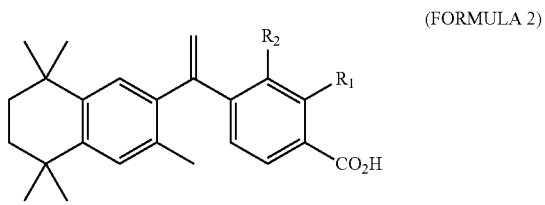

(FORMULA 2)

In the above formula, any of $R_1$-$R_2$ are independently selected from hydrogen, $C_{1\text{-}6alkyl}$, hydroxy, C1-6alkoxy, thiol, halogen, $C(R^6)3$, $CO_2H$, $SO_3H$, $NH_2$, $NHC_{1\text{-}6alkyl}$ or $N(C_{1\text{-}6alkyl})2$. By halogen, it is meant Fl, Br, Cl or I. Where there is more than one halogen moiety at positions $R_1$-$R_2$ the halogens moieties may all be the same or may be different. Specific examples of the compounds of FORMULA 2 are a compound of FORMULA 2 having the following substituents at each of positions R1, and R2:

| Compound # | R1 | R2 |
|---|---|---|
| 8 | H | F |
| 9 | F | H |
| 10 | Cl | H |
| 11 | Br | H |
| 12 | I | H |
| 10a | H | Cl |
| 11a | H | Br |
| 12a | H | I |
| 10b | Cl | Cl |
| 11b | Br | Br |
| 12b | I | I |

In still other embodiments, a preferred compound of the invention has the general formula of FORMULA 3 in which each of the R1 moieties is a halogen.

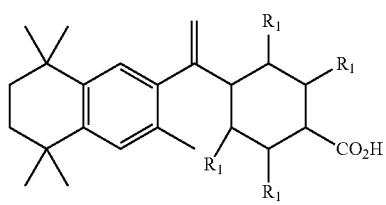

(FORMULA 3)

In specific exemplary embodiments, the compounds of FORMULA 3 are exemplified by compound 13 in which each R1 is F; compound 14 in which each R1 is Cl and compound 14 in which each R1 is Br.

In still other embodiments, a preferred compound of the invention has the general formula of FORMULA 4:

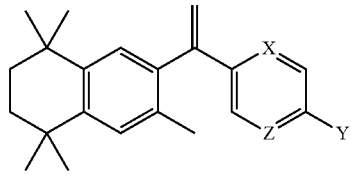

in which X and Z are each independently selected from —CH—, —N—, —S—, or —O—. In specific preferred embodiments, each of X and Z are CH, in other embodiments, each of X and Z are N, in still other embodiments Z is either CH or N and X is either CH or N provided that when Z is CH X is N and when Z is N, X is CH. In any of the foregoing exemplary embodiments, Y is either B(OH)$_2$ or CO$_2$H. Exemplary compounds of FORMULA 4 are compound 16 in which X and Z are both CH and Y is B(OH)$_2$ and compound 17 in which X and Z are both N and Y is CO$_2$H.

In still other embodiments, a preferred compound of the invention has the general formula of FORMULA 5:

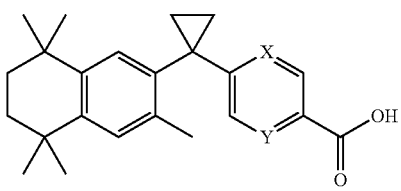

in which X is CH and Y is N or X is N and Y is CH

From the initial modeling and Our preliminary modeling and biological assay results of novel compounds 1-3 and 8-9 indicated that the presence of the carboxylic acid group at its locus in bexarotene is essential for a bexarotene analog's ability to bind, effectively, to RXR. Thus, compounds 1 and 2 did not effectively bind to RXR. Compounds 3 and 8 did bind to RXR, but with lesser affinity than bexarotene, whereas compound 9 displayed a slightly greater affinity than bexarotene. Molecular modeling suggests that restoring the carboxylic acid groups in compounds 4 and 5 will restore the affinity of binding to RXR, and further that compounds 6 and 7, possessing fluorine atoms proximal to the carboxylic acid group, will bind to RXR similar to 8 and 9. Compounds 10-15 will allow the skilled person to systematically gauge the variation of halogen atoms proximal to the carboxylic acid. Compounds 16 and 17 represent novel motifs and may bind to RXR. Finally, compound 18 is of interest, since it is an unreported isomer of LGD100268, and modeling suggests it is a high affinity ligand. Each of these new compounds fall into a general class of RXR-selective agonists that can be associated with one of two classes of preliminary compounds displaying RXR-agonist activity less than or greater than bexarotene.

It has been found that particularly preferred compounds of the invention are halogenated. Thus one example of a preferred compound described herein is a compound of formula 2 in which R1 is F and R2 is H.

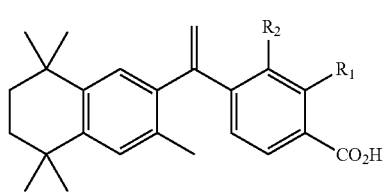

For use in animals and humans for veterinary and medical purposes, the analogs of the present invention may be prepared as salts. Such salts will preferably be non-toxic "pharmaceutically acceptable salt or salts." Other salts may, however, be useful in the preparation of bexarotene analogs of the invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative basic/cationic salts include, but are not limited to, benzathine, chloroprocaine, choline, diethanolamine, ethylenediamine, meglumine, procaine, aluminum, calcium, lithium, magnesium, potassium, sodium, or zinc. The bexarotene analogs of the invention, or a pharmaceutically acceptable salt thereof, may include an intramolecular salt thereof, or a solvate or hydrate thereof.

The bexarotene analogs of the invention may be used as therapeutic agents for any indication in which bexarotene or other RXR agonists are used. For example, the disclosed bexarotene analogs of the invention, compositions comprising the same, and combinations of such compositions with other therapeutic agents will be used in methods for the treatment of hyperproliferative disorders. In specific embodiments such bexarotene analogs of the invention will be particularly useful in the treatment of hyper-proliferative disorders. For example, the hyperproloferative disorder is a cancer. Any cancer that will respond to an RXR agonist may be treated by the analogs described herein. Simply by way of example, the cancer may be a breast, respiratory tract, brain, reproductive organs, digestive tract, urinary tract, eye, liver, skin, head and/or neck, thyroid, parathyroid cancer and/or their distant metastases. For example, the bexarotene analogs described herein will be useful in treating cancers such as lymphoma, sarcoma, or leukemia. The breast cancer treated by the compounds described herein may be an invasive ductal carcinoma, invasive lobular carcinoma, ductal carcinoma in situ, or lobular carcinoma in situ. Respiratory tract cancers such as small-cell lung carcinoma, non-small-cell lung carcinoma, bronchial adenoma or pleuropulmonary blastoma also can be treated by the compounds described herein as can brain cancers such as a tumor of the brain stem, hypophtalmic glioma, cerebellar astrocytoma, cerebral astrocytoma, medulloblastoma, ependymoma, neuroectodermal or pineal tumor. The compounds also may be used in the treatment of a tumor of the male reproductive organ is a prostate or testicular cancer or a cancer of the female reproductive organ is endometrial, cervical, ovarian, vaginal, vulvar, or sarcoma of the uterus. Cancer of the digestive tract such as anal cancer, colon cancer, colorectal cancer, esophageal cancer, gallbladder cancer, gastric cancer, pancreatic cancer, rectal cancer, small-intestine cancer or salivary gland cancer can also be treated by the analogs described herein. The cancer to be treated also may be aurinary tract cancer such as a cancer of the bladder, penile, kidney, renal pelvis, ureter or urethral. Eye cancers such as intraocular melanoma or retinoblastoma also may be treated by the analogs of the invention. Liver cancer such as hepatocellular carcinoma, liver cell carcinomas with or without fibrolamellar variant, cholangiocarcinoma or mixed hepatocellular cholangiocarcinoma also may be treated. Skin cancers such as squamous cell carcinoma, Kaposi's sarcoma, malignant melanoma, Merkel cell skin cancer or non-melanoma skin cancer may be treated with the compounds described herein. Head and neck cancer such as laryngeal, hypopharyngeal, nasopharyngeal, oropharyngeal, lip or oral cavity cancer also may be treated with the compounds of the invention. The compounds may be used to treat AIDS AIDS-related lymphoma, non-Hodgkin's lymphoma, cutaneous T-cell lymphoma, Hodgkin's disease or lymphoma of the central nervous system, a sarcoma of the soft tissue, osteosarcoma, malignant fibrous histiocytoma, lymphosarcoma or rhabdomyosarcoma. Leukemias such as acute myeloid leukemia, acute lymphoblastic leukemia, chronic lymphocytic leukemia, chronic myelogenous leukemia or hairy cell leukemia may be treated using the compounds of the invention. Each of these cancers may benefit from treatment with the analog compounds of the invention alone or treatment with the compounds of the invention in combination with other chemotherapeutic agents or anti-cancer therapies.

In other embodiments, the bexarotene analogs of the invention may be used to treat other disorders that involve modulation of RXR and in particular that involve agonism of RXR. Such other disorders are those that are typically treatable by bexarotene, and include for example dyslipidemia, hyperlipidemia, hypercholesteremia, atherosclerosis, atherogenesis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs (irritable bowel disease), ulcerative colitis and Crohn's disease and the like. In the therapeutic methods, the bexarotene analogs of the invention may be administered to a patient by any conventional route of administration, including, but not limited to, intravenous, oral, subcutaneous, intraocular intramuscular, intradermal and parenteral administration. Preferably, formulations are for oral administration.

The present invention also provides pharmaceutical compositions comprising one or analogs of the present invention and one or more other RXR modulators or other therapeutic agents in association with a pharmaceutically acceptable carrier.

The daily dosage of the products may be varied over a wide range from 1 to 1000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 or 500 milligrams of the active ingredient for the symptomatic adjustment of the dosage to the patient to be treated. The analogs of the present invention may be administered on a regimen of 1 to 2 times per day. The dosages, however, may be varied depending upon the requirement of the patients, the severity of the condition being treated and the compound being employed. The use of either daily administration or postperiodic dosing may be employed. Preferably these compositions comprising the analogs of the present invention are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient or ingredients are mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of one or more analogs of the present invention or a pharmaceutically acceptable salt thereof. When referring to these preformulation compositions as homogeneous, it is meant that the active ingredient or ingredients are dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient or ingredients of the present invention. The tablets or pills of the analogs of the present invention can be coated or otherwise compounded to provide a dosage form affording the advantage of sustained release or prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

In other embodiments, the analogs of the present invention may be provided in liquid forms in which the analogs of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methylcellulose and the like.

For parenteral administration, sterile suspensions and solutions are desired. Isotonic preparations which generally contain suitable preservatives are employed when intravenous administration is desired.

The compositions comprising the analogs of the present invention or pharmaceutically acceptable salts thereof may be administered in a single daily dose, or the total daily dosage may be administered in divided doses of two, three or four times daily.

For oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

In embodiments in which the analogs of the present invention are administered as part of a combination therapy, the analogs of the present invention may be co-administered with the second therapeutic agent simultaneously, sequentially, or in a single pharmaceutical composition. Where the compounds are administered separately, the number of dosages of each compound given per day, may not necessarily be the same, e.g. where one compound may have a greater duration of activity, and will therefore, be administered less frequently.

Exemplary chemotherapeutic agents that can be used in combination therapies with compositions comprising the analogs of the presented invention include but are not limited to bexarotene, cyclophosphamide, mechlorethamine, mephalin, chlorambucil, heamethylmelamine, thiotepa, busulfan, carmustine, lomustine, semustine, methotrexate, fluorouracil, floxuridine, cytarabine, 6-mercaptopurine, thioguanine, pentostatin, vincristine, vinblastine, vindesine, etoposide, etoposide orthoquinone, and teniposide, daunorubicin, doxorubicin, mitoxantrone, bisanthrene, actinomycin D, plicamycin, puromycin, and gramicidine D, paclitaxel, colchicine, cytochalasin B, emetine, maytansine, and amsacrine, aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-fluorouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, Mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. This is merely an exemplary list and those skilled in the art will understand that the analogs of the presented invention, being suitable therapeutic agents for treating any disorder that can be treated by bexarotene, may be combined with any therapeutic agent that is used to treat a disorder that is treatable by bexarotene (commercially available as Targretin®).

Other therapeutic agents that are used in the treatment of metabolic disorders such as dyslipidemia, hyperlipidemia, hypercholesteremia, atherosclerosis, atherogenesis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs (irritable bowel disease), ulcerative colitis and Crohn's disease may be combined with the bexarotene analogs of the present invention. Such therapeutic agents include estrogen, testosterone, a selective estrogen receptor modulator, a selective androgen receptor modulator, insulin, insulin derivatives and mimetics; insulin secretagogues such as the sulfonylureas, e.g., Glipizide and Amaryl; insulinotropic sulfonylurea receptor ligands, such as meglitinides, e.g., nateglinide and repaglinide; insulin sensitizers, such as protein tyrosine phosphatase-1B (PTP-1B) inhibitors, GSK3 (glycogen synthase kinase-3) inhibitors or RXR ligands; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors, e.g. isoleucin-thiazolidide; DPP728 and LAF237, hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (liver X receptor) and LXR (farnesoid X receptor) ligands, cholestyramine, fibrates, nicotinic acid and aspirin. A bexarotene analog of the present invention may be administered either simultaneously, before or after the other active ingredient, either separately by the same or different route of administration or together in the same pharmaceutical formulation.

Optimal dosages to be administered will likely be determined on a case-by-case basis and will be readily determined by those skilled in the art. Such dosing will typically vary with the particular compound used, the strength of the preparation, the mode of administration, and the advancement of the disease condition. In addition, factors associated with the particular patient being treated, including patient age, weight, diet and time of administration, will result in the need to adjust dosages.

The analogs of the present invention and pharmaceutically acceptable salts thereof can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof.

Also contemplated herein is a pharmaceutical combination kit, comprising: a) a first agent which is a bexarotene analogs of the present invention, in free form or in pharmaceutically acceptable salt form, and b) at least one co-agent. The kit can comprise instructions for its administration.

EXAMPLES

Preliminary Studies

An initial array of bexarotene analogs comprising compounds 1-3, and their corresponding ketone derivatives (compounds 30-32) [as well as 8, 8b, 9, 9b, and 33a] were targeted for synthesis and evaluation for their ability to selectively bind to RXR.

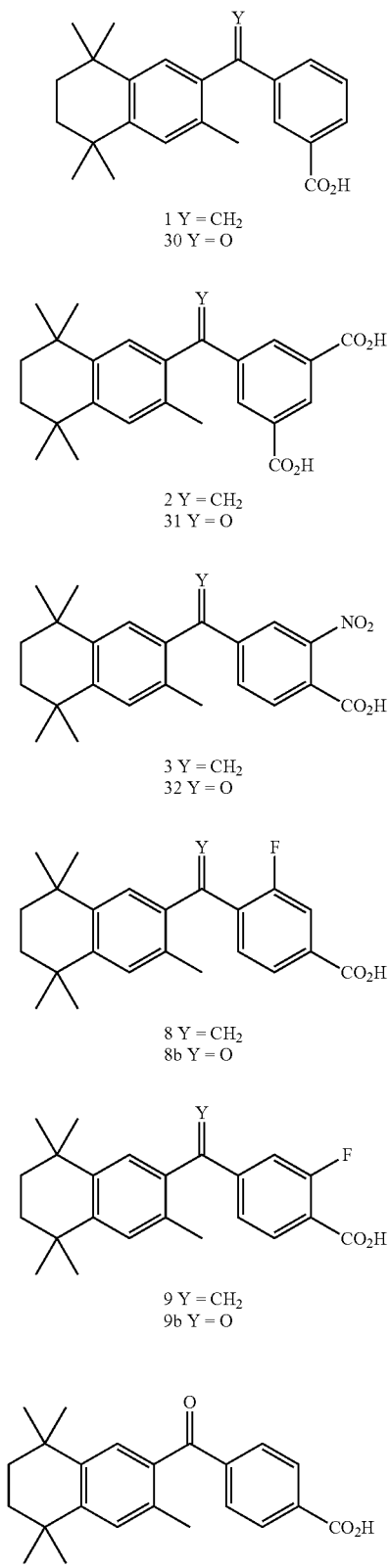

In order to efficiently screen the synthesized analogs for initial binding to the RXR receptor protein, a mammalian cell two-hybrid assay was developed was used. The gene for human RXRα was first cloned into a vector containing either the DNA binding domain of GAL4 (RXR-BD) or the transcriptional activation domain of NF-κB (RXR-AD). Human colon cancer cells (Caco-2) were then transfected with both of these constructs (and appropriate controls) via liposome-mediated technology.

The cells were also transfected with a "reporter" vector that contains five tandem copies of the GAL4 DNA binding site upstream of the gene for Firefly luciferase. In this system, any compound that can bind to RXR and induce RXR homodimerization will cause induction of the luciferase reporter gene that is then assayed using a standard commercially available luciferase enzyme kit (Promega Corporation). The level of luciferase activity in the lysates from the transfected Caco-2 cells treated with the bexarotene analogs serves as a direct index of the level of homodimerization, and therefore of the affinity of the analog for RXR within the cellular context of Caco-2 (FIG. 1).

The eleven compounds shown above have been examined in the mammalian two-hybrid assay. Despite the fact that ketone 30 has been documented as an inactive compound, and our modeling studies also suggest that compound 1 is a low affinity ligand for RXR, the fact that the ketone derivative of bexarotene (33a) is an order of magnitude less active than bexarotene as well as an opportunity to validate our model motivated the synthesis and evaluation of compound 1. Further, the addition of a second carboxylic acid functional group in bexarotene analogs 2 and 31 generated candidates of interest. In the case of 31, the interest concerned whether the additional carboxylic acid group would restore selective binding and activation that was reported lacking in 30. A nitrobexarotene analog (3) and its corresponding ketone derivative (32) were two initial targets of interest, since each compound preserved the original position of the carboxylic acid group in bexarotene while adding an electron withdrawing nitro group ortho to the carboxylic acid. Finally, the fluorinated bexarotene analogs, 8, 8b, 9, and 9b were prime candidates of interest, since the addition of fluorine to other RXR agonists showed augmented agonism.

Biological evaluation of these initial analogs employing the mammalian two-hybrid assay (FIG. 1) revealed that compounds 3, 8, and 9 exhibited activity on the same order of magnitude as bexarotene. [More importantly, the initial array of analogs show a range of binding/transcription ability: 3 and 8 bind and mediate transcription about as well as bexarotene, whereas compound 9 binds and activates transcription better than bexarotene, on average. Additionally, ketones 9b and 33a also show a small degree of binding and transcription relative to bexarotene. From these preliminary data stems the incentive to construct additional bexarotene analogs that preserve the carboxylic acid position but substitute non-hydrogen atom groups on the aromatic ring that bears the carboxylic acid. The approach described should enable the fine-tuning of the agonist character of the molecule, and such analogs may induce unique interaction of RXR with other heterodimerizing nuclear receptors, thereby attenuating unwanted side effects such as antagonism of the RXR-TR pathway that likely causes the hypothyroidism observed in some patients.

In addition to the two-hybrid screening for agonist binding to RXR, the RXR agonists were tested for their role of the correct biologically relevant DNA platform, or retinoid X receptor response element (RXRE), that specifically associates with the RXR homodimer in vivo. The RXRE DNA sequence is present in the upstream promoter region of genes controlled by the RXR homodimer in response to the endogenous 9-cis RA ligand, or when RXR is bound to a synthetic rexinoid. It is possible that the RXRE may influence the affinity and/or selectivity of the RXR protein towards potential ligands. Thus, a second screening protocol for the collection of possible RXR agonists of the invention includes transfection of human Caco-2 cells with an expression vector for wild-type human RXRα along with a reporter construct that contains an RXRE based on a naturally occurring double repeat response element from the cellular retinol binding protein II gene.

A successful RXRα/RXRE-reporter system in Caco-2 cells which is responsive to the bexarotene RXR agonist (FIG. 2) has been developed and will continue to be employed in testing the complete panel of potential RXR ligands.

For comparison in the biological evaluation (FIGS. 1 and 2) of compounds 1-3, [8 and 9] and 30-32, [8b and 9b] an authentic sample of bexarotene and its ketone analog (33a) were synthesized, following the reported route (Boehm, et al. "Synthesis and Structure-Activity Relationships of Novel Retinoid X Receptor-Selective Retinoids." J. Med. Chem. 1994, 37, 2930-2941): a seven step, convergent synthesis that gave a 29% overall yield of bexarotene. The first sequence of steps to bexarotene concerned the SN1 conversion of 2,5-dimethyl-2,5-hexanediol (33b) to 2,5-dichloro-2,5-dimthyl-hexane (34) by HCl, and the subsequent aluminum trichloride catalyzed Friedel-Crafts alkylation of toluene to give 1,2,3,4-tetrahydro-1,1,4,4,6-pentamethylnapthalene (35) in 68% yield over two steps (Scheme 1).

SCHEME 1

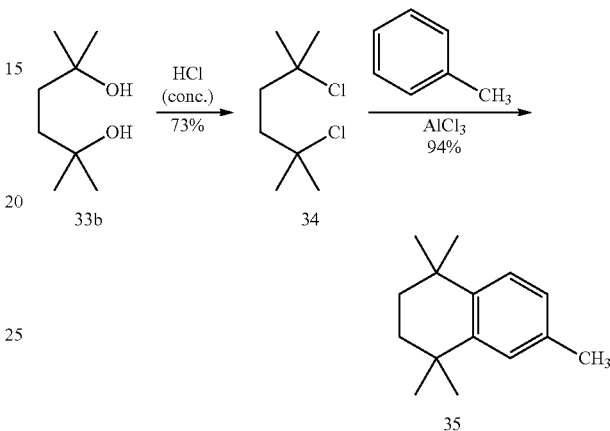

Rectangular plates of compound 35 were found suitable for X-ray diffraction, and a study was conducted. To complete the synthesis of bexarotene, the Friedel-Crafts acylation of 35, by crude mono-methyl-terephthaloyl chloride (36), gave ketone (37) which was converted to alkene ester (38) by a Wittig reaction, and ester 38 was saponified by potassium hydroxide followed by acidification with aqueous hydrochloric acid to give bexarotene (39) (Scheme 2).

Scheme 2

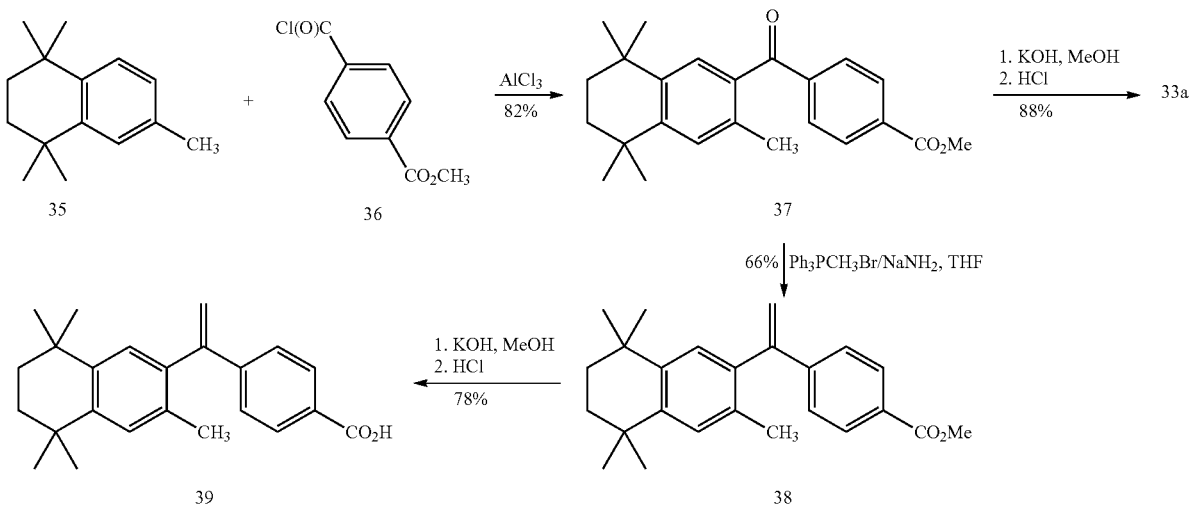

The chemical steps in Schemes 1 and 2 were modified to create analogs 1-3. For example, analog 1 was synthesized by the Friedel-Crafts acylation of 35 by mono-methyl isophthaloyl chloride (40) to give ketone 41 which was either subsequently converted to the alkene ester (42) or the ketone acid (30). The alkene ester 42 was subsequently converted to the carboxylic acid analog (1) with potassium hydroxide followed by acidification with HCl (Scheme 3).

-continued

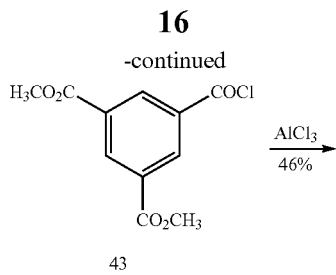

SCHEME 3

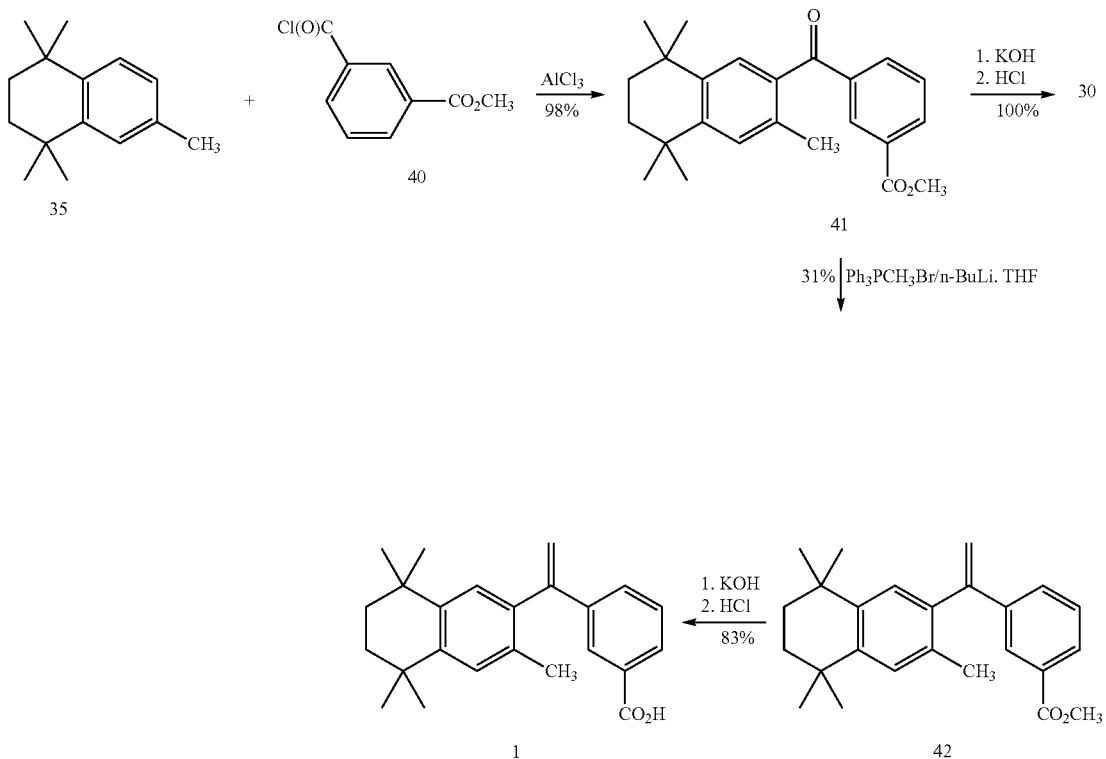

Analog 1 formed crystals suitable for X-ray diffraction, and the structure is shown. The mono-methyl isophthaloyl chloride can be prepared from the commercially available mono-methyl isophthalate by refluxing in excess thionyl chloride.

In a similar synthetic manner, analogs 2 and 31 were synthesized (scheme 4)

SCHEME 4

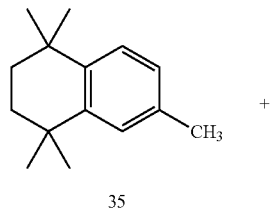

-continued

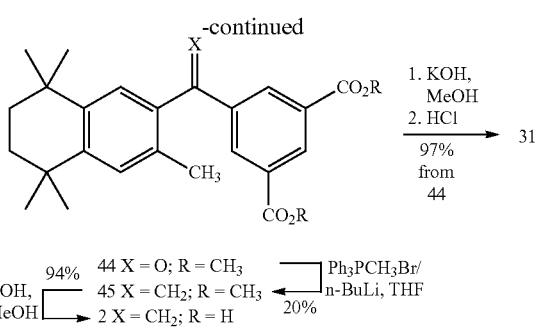

Compound 35 underwent the Friedel-Crafts acylation with acid chloride (43) to give ketone diester (44) in 46% yield. The ketone diester 44 was converted to analog 31 in near quantitative yield or it was converted to the alkene diester (45) and thence to analog 2 in 19% yield over two steps. The acid chloride (43) was prepared as follows. Trimethyl-1,3,5-benzenetricarboxylate (46) was converted to the mono-acid diester (47) according to literature procedures (Dimick, et al. "On the Meaning of Affinity: Cluster Glycoside Effects and Concanavalin A" J. Am. Chem. Soc. 1999, 121, 10286-10296), and compound 47 was refluxed in excess thionyl chloride to give acid chloride 43 (Scheme 5).

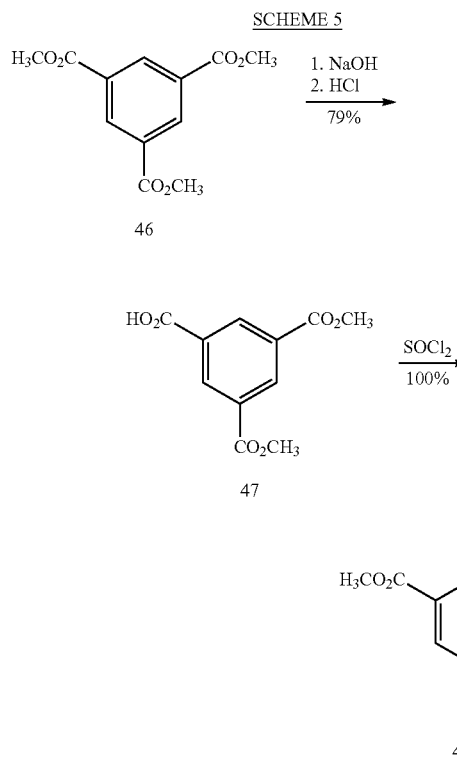

Compounds 47 and 43 from Scheme 5 were used for the synthesis of analogs 2 and 31.

Analog 3, with a nitro group ortho to the carboxylic acid, was synthesized in a similar manner as analogs 1 and 2 (Scheme 6)

Again, compound 35 underwent the Friedel-Crafts acylation with acid chloride (48) to give ketone ester (49) in 87% yield. The ketone ester 49 was converted to analog 32 in quantitative yield or it was converted to the alkene ester (50) and thence to analog 3 in 9% yield over two steps. When the deprotonation of methyltriphenylphosphonium bromide was attempted with sodium amide in the Wittig reaction to convert 49 to 50, no alkene product was observed. Nitro-aromatics have been reported to react with both sodium amide (Gandi, "Reactions of Some Aromatic Nitro Compounds with Alkali Metal Amides" J. Org. Chem. 1979, 44, 4705-4707) and ylides (Treynelis, "Ylide Methylation of Aromatic Nitro Compounds" J. Org. Chem. 1966, 31, 243-247), so it was surprising that the use of n-butyl lithium in the Wittig reaction provided the alkene 50 from ketone 49, albeit in 11% yield. The acid chloride (48) was prepared by first converting dimethyl-nitro-terephthalate (48) to the mono-acid ester (52) according to literature procedures (Keenan, et al. "Conformational Preferences in a Benzodiazepine Series of Potent Non-peptide Fibrinogen Receptor Antagonists" J. Med. Chem. 1999, 42, 545-559), and then refluxing compound 52 in excess thionyl chloride (Scheme 7).

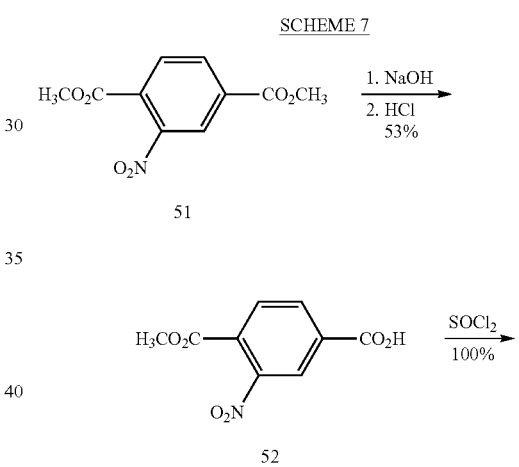

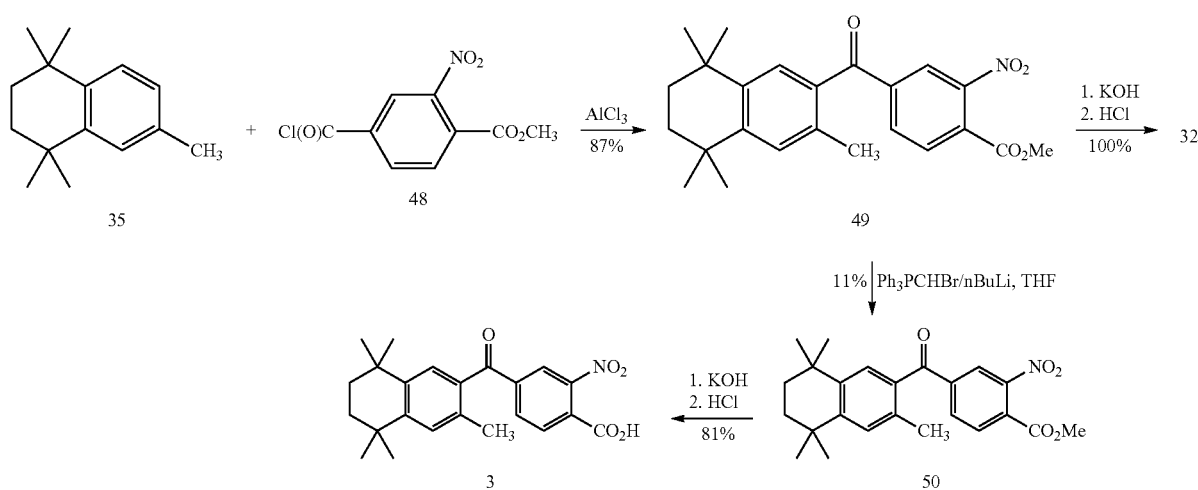

-continued

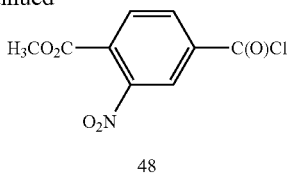

48

Progress in the proposed synthesis of analog 16 is as follows. Compound 35 was successfully acylated with boronic ester acid chloride (53) to give the ketone boronic acid (54) in 47% yield after aqueous workup, and 54 was converted to the boronic ester (55) in quantitative yield treatment with 1,3-propanediol in refluxing toluene (Scheme 8).

Crystals of ketone boronic ester (55) were suitable for X-ray diffraction. The boronic ester acid chloride (53) was prepared as follows. Commercially available 4-carboxyphenylboronic acid (56) was converted to boronic ester (57) according to literature procedures (Takahasi et al. "2,5-Diaryl-1,3,2-dioxaborinanes: A New Series of Liquid Crystals" Bull. Chem. Soc. Jpn. 1989, 62, 3896-3901) in 96% yield, and 57 was refluxed in excess thionyl chloride to give acid chloride (53) (Parry, D.; Papon, J.; Moins, N.; Moreau, M.-F.; Morin, C. "A Boronated Benzamide As Melanoma-Seeking Agent" Biorg. Med. Chem. Lett. 1997, 7, 361-364) (Scheme 9).

SCHEME 8

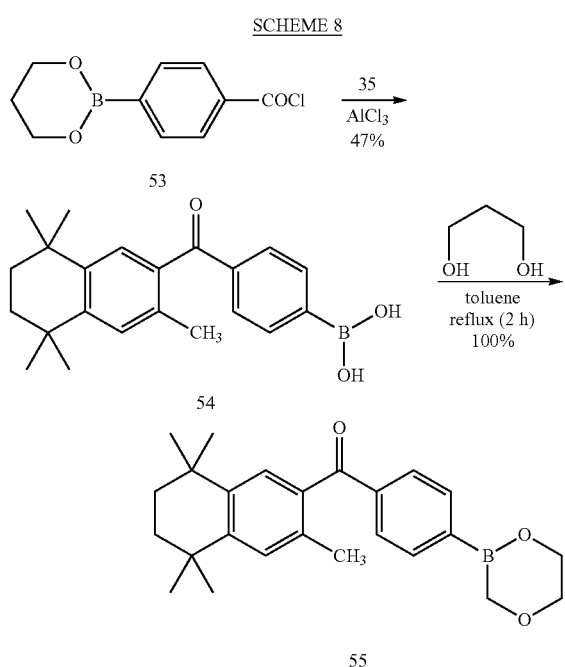

SCHEME 9

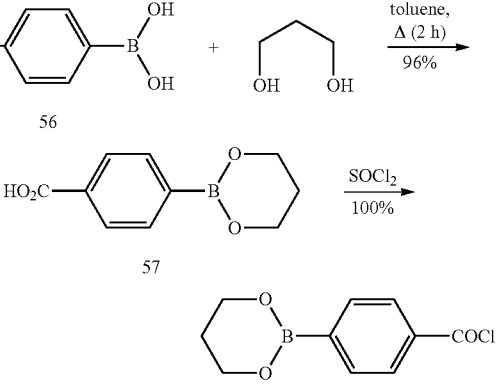

Progress toward analog 18 has been made as follows. 2,5-Pyridinedicarboxylic acid (58) was preferentially esterified according to literature protocols66 by reflux in methanol with catalytic sulfuric acid for 2 hours to the mono-methyl ester (59) in 42% recovered yield after recrystallization from water. The monomethyl ester 59 was refluxed in excess thionyl chloride to effect its conversion to the acid chloride (60), and 60 was used to acylate 35 by reflux in DCM with excess aluminum trichloride (Scheme 10).

SCHEME 10

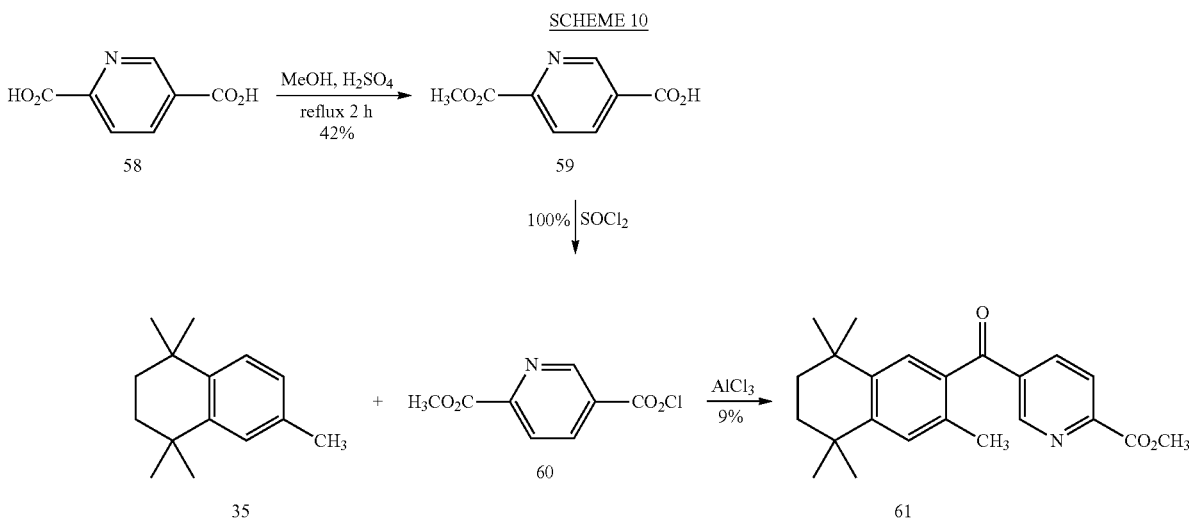

Crystals of 59 from methanol were suitable for X-ray diffraction. The low yield of the ketone ester (61) in the acylation reaction may arise from reflux, since a 50% yield was reported for the isomeric ketone derivative of alkene (25) in its reported synthesis conducted at room temperature.

Finally, compounds 8, 8b, 9, and 9b were synthesized by converting the reported 4-(methoxycarbonyl)-2-fluorobenzoic acid (62) and 4-(methoxycarbonyl)-3-fluorobenzoic acid (63) to acid chlorides 64 and 65, respectively. The acid chlorides 64 and 65 were used to acylate 35 and give ketones 66 and 67, respectively, which were converted either to carboxylic acids 8b and 9b or alkene-esters 68 and 69. The alkene-esters 68 and 69 were saponified to fluorinated-bexarotene analogs 8 and 9 (Scheme 11). Both compounds 8 and 9 formed crystals suitable for X-ray diffraction studies, and the X-ray crystal structures of 8 and 9 were obtained.

Figure 2:
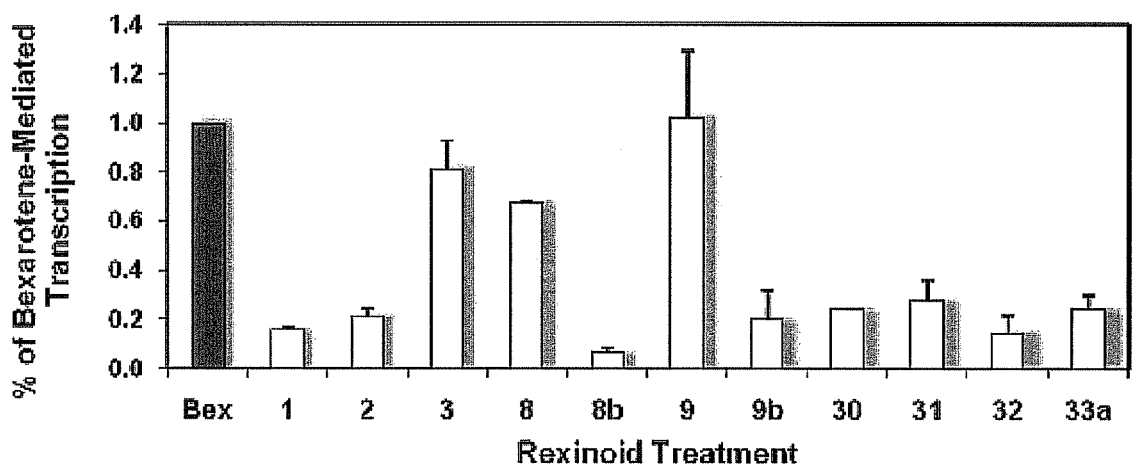
FIG. 2: Identification of potential RXR agonists via an RXRE-luciferase reporter-based screening assay in human colon cancer cells.

Docking studies (FIG. 3) of compounds 1-3, 8 and 9 revealed reasonable agreement with preliminary experimentally measured binding as assessed by the mammalian two-hybrid and RXRE-based assays (FIGS. 1 and 2). The protein structure for the docking studies was taken from the X-ray structure of the human RXRα ligand-binding domain in complex with the BMS649 ligand87; the framework of this ligand is similar to compounds 1-18. To enable hydrogen bonding between the carboxylic acid groups of the ligand and the protein, the docking studies fully optimized the side chain of Arg316, while keeping the rest of the protein rigid. The calculations predicted low affinities for compounds 1 and 2, and high affinities for 8 and 9, while overestimating the affinity for compound 3.

Figure 3:
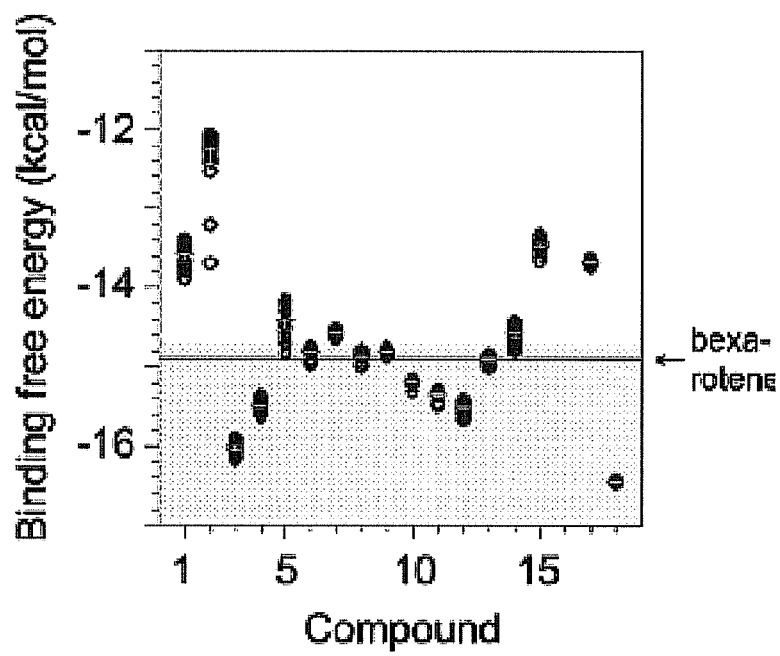
FIG. 3: Binding free energies of compounds 1-15, 17-18 as predicted from docking studies to the human RXRα ligand binding domain. The 20 best solutions are shown for each ligand, the averages and standard deviations are shown by the magenta bars. Ligands that are expected (not) to bind are shown in (red) green; as an approximate criterion for binding, we used a value of 1 kcal/mol above the calculated binding free energy of bexarotene.

The results of the docking studies for proposed compounds 4-7, 10-15, 17 and 18 are also shown in FIG. 3; data for 16 is

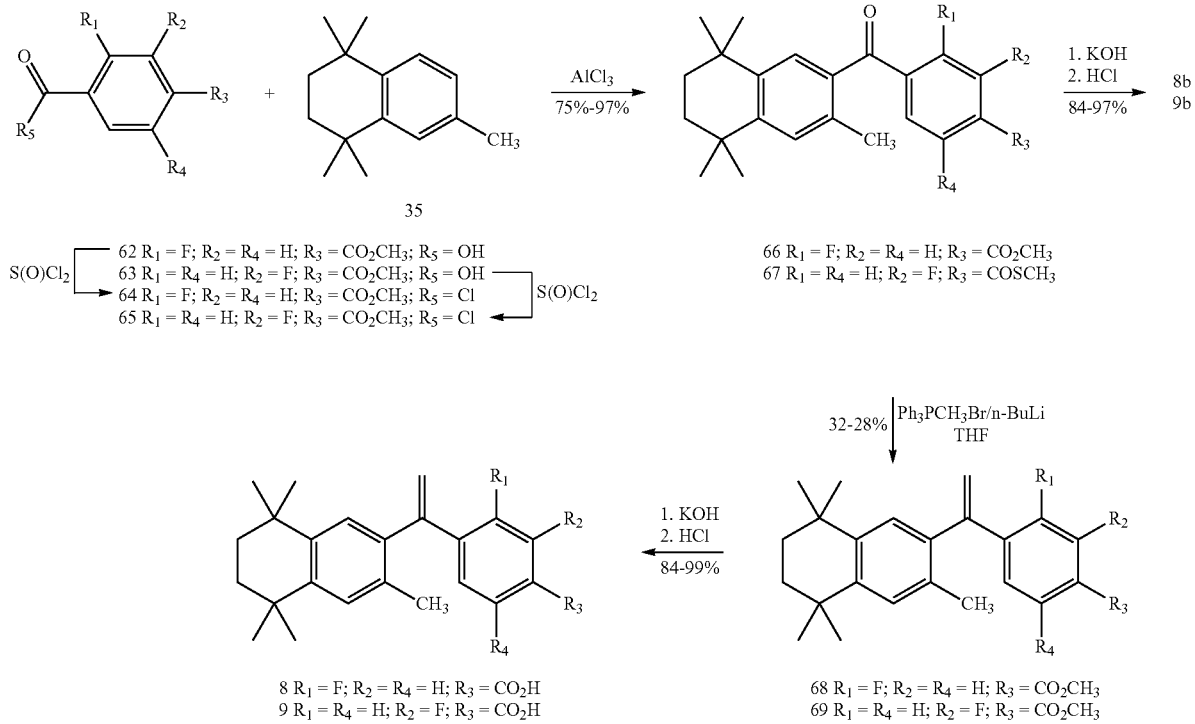

SCHEME 11

The synthesized analogs have been tested for mutagenicity and toxicity in an eukaryotic in vivo assay. The in vivo assay utilizes *Saccharomyces cerevisiae* as the tester strain and simultaneously detects reversion mutations and DNA damage that leads to homologous recombination repair or gene conversion. If the DNA is mutated by the test compound and then subsequently repaired, the strain demonstrates certain phenotypes in response to genotype change. These phenotypes are scored as colony sectoring and growth on dropout media. This is an Environmental Protection Agency approved assay (Mitotic Gene Conversion in *Saccharomyces cerevisiae*) used to test pesticides and other toxic substances. Clearly, a mutagenic compound would have limited usefulness as a human therapeutic, and thus these assays were critical in determining the suitability of these compounds. Using this assay, compounds 1-3, 30-32, and 8, 9, 8b, and 9b were tested. The compounds, including the starting compound bexarotene, were assayed in increasing concentrations for mutagenicity. None of the compounds was mutagenic.

lacking due to the absence of parameters for a boronic acid functional group. With the exception of 15 and 17, the proposed compounds are predicted to bind with similar or better affinities than bexarotene. Of particular interest are compound 4, 10-12 and 18, which are predicted to have the lowest binding free energies but have not yet been tested in our biological assays.

Figure 4:
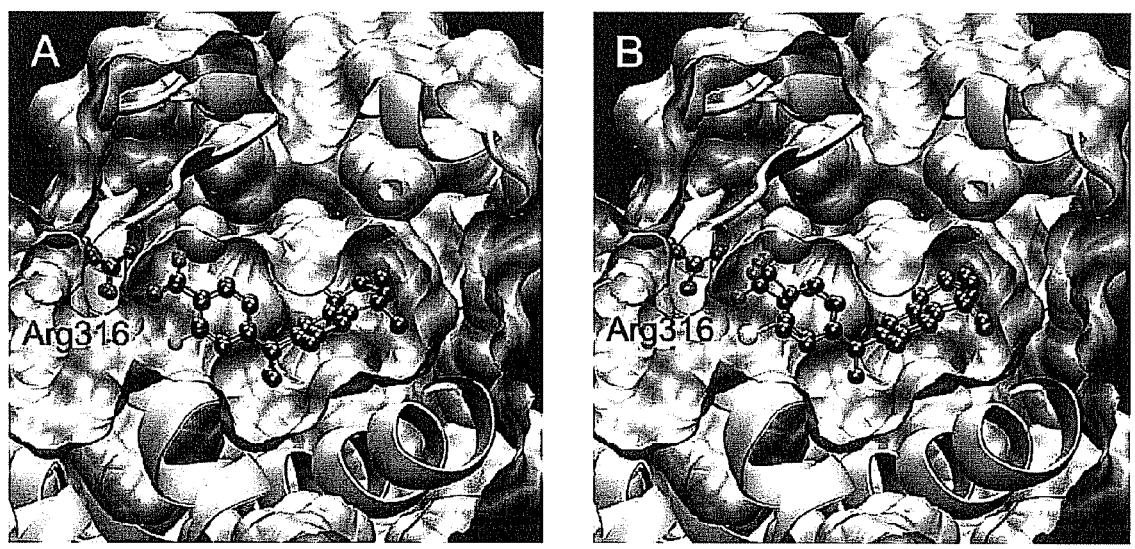
FIG. 4: Docked structures of 9 (A) and 12 (B): in both cases, the docked bexarotene structure is shown as well.

Analysis of the docking results shows that the differences in binding are mostly due to variations in desolvation and electrostatic energies; the overall structures of the docked complexes are very similar. FIG. 4 illustrates the docked structure of compound 9 (A) and 12 (B); in both cases the lowest energy structures are overlayed with the docked structure of bexarotene. As the figure shows, the orientation and binding mode of the ligands is markedly similar. The binding pocket is almost entirely hydrophobic, except for the Arg316 residue which hydrogen bonds to the carboxylate groups of the ligands. Our preliminary docking studies show the binding potential of the proposed compounds, providing a compelling motivation to pursue the synthesis and biological evaluation of these analogs.

Example 2

Synthesis the Bexarotene Analogs

The following example provides additional description of synthesis and purification of additional potential RXR selective agonists. Analogs 4 and 5 represent novel bexarotene analogs that may be able to modulate the conformation of RXR by placing additional carboxylic acid groups in proximity (ortho) to the carboxylic acid group of bexarotene that is vital to it's ability to bind to RXR and act as an agonist. Analogs 4 and 5 can be synthesized in a similar manner as analog 2, but starting from, respectively, the reported diester 70 and triester 71, derived from the reported tetraester 72.

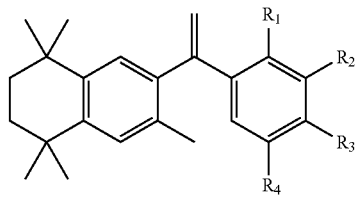

4 $R_1 = R_4 = H$, $R_2 = R_3 = CO_2H$
5 $R_1 = H$, $R_2 = R_3 = R_4 = CO_2H$

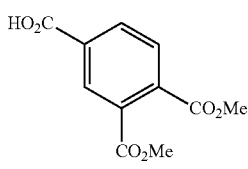

70

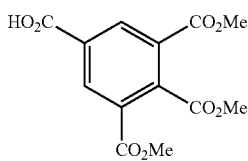

71

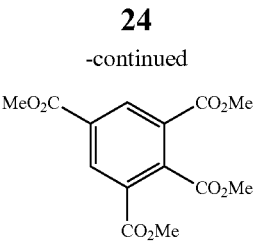

72

Commercially available trimethyl-1,2,4-benzenetricarboxylate will be selectively mono-demethylated with N,N-dimethylhydrazine to give diester 70 that will subsequently be treated with thionyl chloride to give acid chloride 73 (Scheme 12).

SCHEME 12

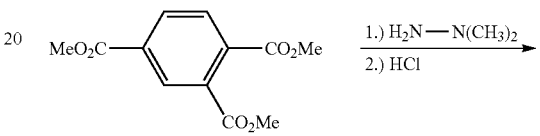

Trimethyl-1,2,4-benezenetricarboxylate

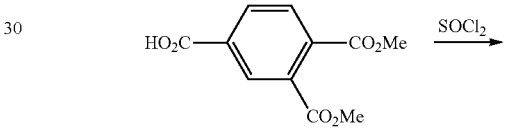

70

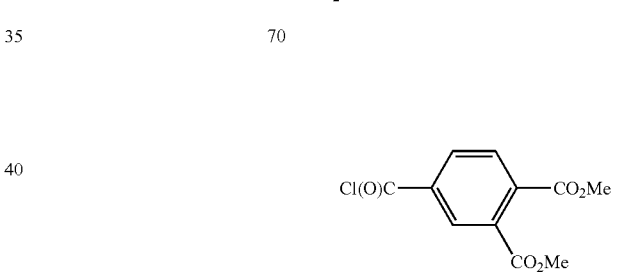

73

The acid chloride 73 will then be used in the Friedel-Crafts acylation of compound 35 to give ketone 74 that will be either converted to diacid 75 or used in the Wittig reaction to give alkene 76 which can be transformed to analog 4 (Scheme 13).

SCHEME 13

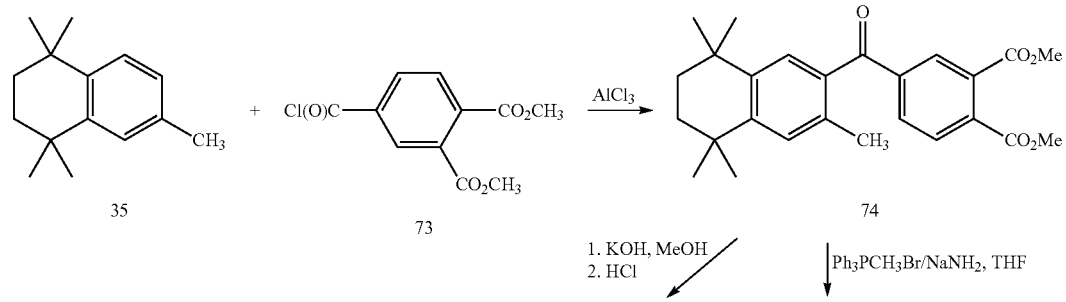

-continued

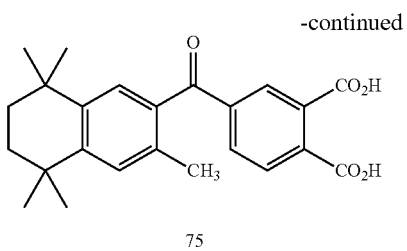

75

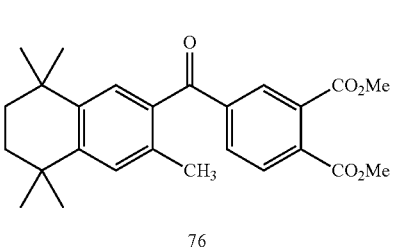

76

1. KOH
2. HCl
→ 4

Triester 71 may be synthesized in a manner similar to the diester 70 (Scheme 12), and thus analog 5 may be constructed in a manner similar to the synthesis of 4 (Scheme 13).

Bexarotene analogs 6 and 7 are of interest to probe whether the addition of multiple fluorine atoms to the carboxylic acid group will still display binding as strong as compound 9 in the LBD of RXR. There is evidence that the arginine residue (Arg387) can extend with flexibility (~2 Angstroms) into the LBD of hRXR55 to form a salt bridge with the carboxylic acid of LG100268, and thus the inventors are encouraged to explore whether a hydrogen bonding interaction with a fluorine group can be established in analogs 6 and 7.

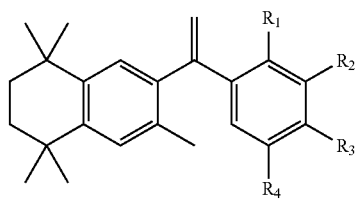

6 $R_1 = R_2 = F$, $R_3 = CO_2H$, $R_4 = H$
7 $R_1 = H$, $R_2 = R_4 = F$, $R_3 = CO_2H$

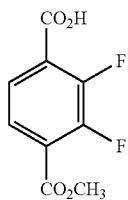

77

-continued

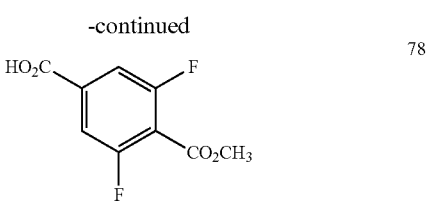

78

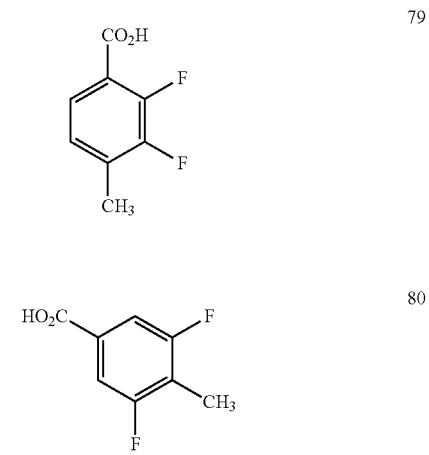

79

80

It is expected that analogs 6 and 7 can be synthesized from the difluoro-monomethylterephthalic acids 77 and 78 derived from commercially available 2,3-difluoro-4-methylbenzoic acid (79) or the reported 3,5-difluoro-4-methylbenzoic acid (80) according to similar methodology for the synthesis of compounds 62 and 63. For instance, with compound 77 in hand, we would convert 77 to acid chloride 81 that we would use to acylate compound 35 to give ketone 82. The ketone compound ketone 82 could be converted to di-acid 83 or the Wittig reaction can be performed to convert ketone 82 to the alkene-ester 84 that could then be saponified to analog 6 (Scheme 14)

SCHEME 14

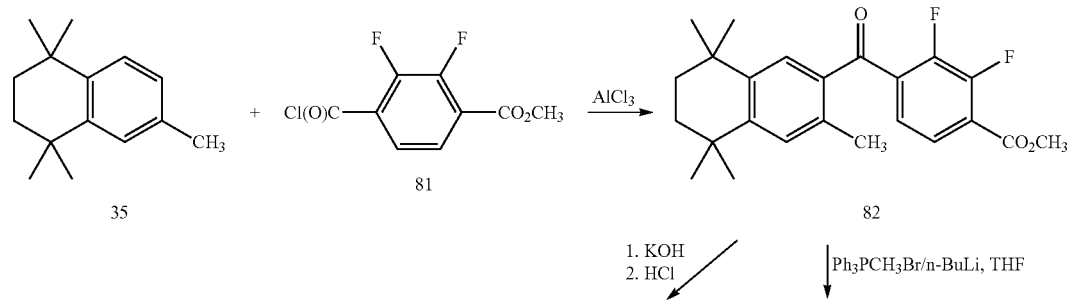

1. KOH
2. HCl

Ph₃PCH₃Br/n-BuLi, THF

-continued

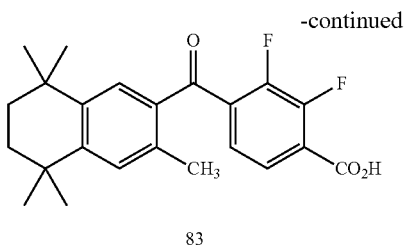

83

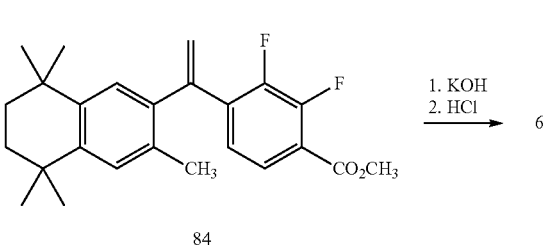

84

1. KOH
2. HCl
→ 6

It is contemplated that synthesis of analog 7 would proceed in a similar manner to analog 6.

Analogs 10-12 are novel bexarotene analogs that will permit evaluation of the effects of the addition of different halogen atoms to the aromatic ring that bears the carboxylic acid group. It is expected that the addition of fluorine will increase affinity for binding as reports of the addition of fluorine to other RXR agonist molecules have attested. It is contemplated that analogs 10, 11, and 12 to be constructed from the reported acids 85, 86, and 87, respectively.

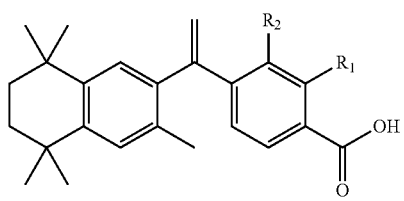

10 $R_1$ = Cl, $R_2$ = H
11 $R_1$ = Br, $R_2$ = H
12 $R_1$ = I, $R_2$ = H

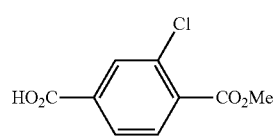

85

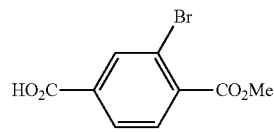

86

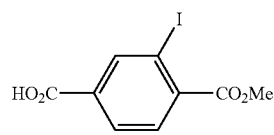

87

It is also contemplated that the synthesis of analogs 10-12 will follow the same methodology exemplified by the synthesis of 8 and 9 (Scheme 11) additional experimental observations relating to modeling results for compound 12 will be conducted to see if these correspond to observations of a high affinity, strongly activating ligand. Bexarotene analogs 13-15, substituting all the hydrogen atoms with halogen atoms on the aromatic ring bearing the carboxylic acid will be useful to compare to the mono-halogenated analogs 8-12. It is contemplated that a synthesis of analogs 13-15 following the representative synthetic scheme described for analog 9 (Scheme 14) and starting from the acid chlorides derived from mono-methyl-tetrahalogenated terphthalates 88, 89, and 90.

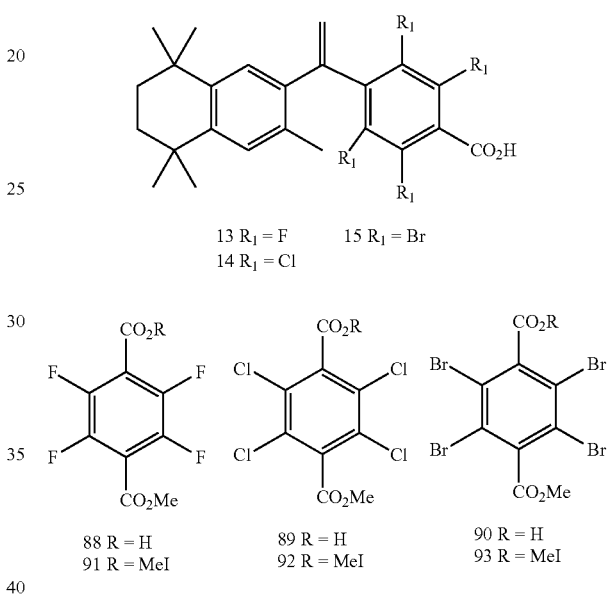

13 $R_1$ = F     15 $R_1$ = Br
14 $R_1$ = Cl

88 R = H         89 R = H         90 R = H
91 R = MeI       92 R = MeI       93 R = MeI

The mono-methyl-tetrahalogenated terphthalates 88-90 are envisioned to be accessible from the monoazine acid ester (94) that should be accessible from the ported 2,5-bis-methoxycarbonylpyrazine (95) demethylation of the reported dimethyl-tetrahalogenated-terphthalates 91, 92, and 93. Novel bexarotene analogs 16 and 17 are of interest, since 16 replaces the carboxylic acid group of bexarotene with a boronic acid and 17 incorporates a novel pyrazine ring. We hypothesize that the analog 16 will bind RXR and act as an agonist, since carboxylic acids on bioactive compounds have been successfully substituted with boronic acids, and there is one example of an FDA approved drug (Bortezomib) containing a boronic acid that was demonstrated as a proteasome inhibitor. It is predicted that analog 17 will bind to RXR and act as an agonist, since several bexarotene analogs with structurally similar pyridyl rings have been demonstrated to be potent agonists. The novel pyrazine ring system of analog 17 may elicit different conformational effects on RXR, as the close contact amino acid residues in the ligand binding domain may experience different affinities for the pyrazine ring than the bexarotene analogs containing pyridyl rings. The synthesis of analog 16 will be from the advanced intermediate 55. Similarly, the synthesis of analog 17 also may be from the pyrazine acid ester that should be accessible from the reported 2,5-bismethoxycarbonylpyrazine (95).

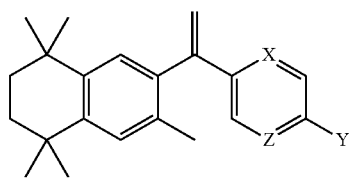

16 X = Z = CH, Y = B(OH)₂
17 X = Z = N, Y = CO₂H

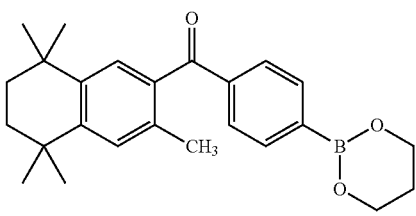

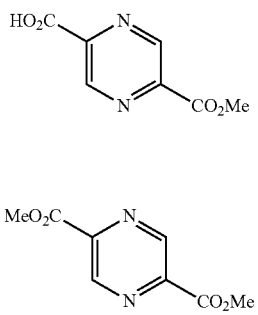

For example, the Wittig reaction of triphenylphosphonium methylide with the ketone boronic ester 55 should provide the alkene boronic ester 96 which can be converted to analog 16 by potassium hydroxide (Scheme 15).

SCHEME 15

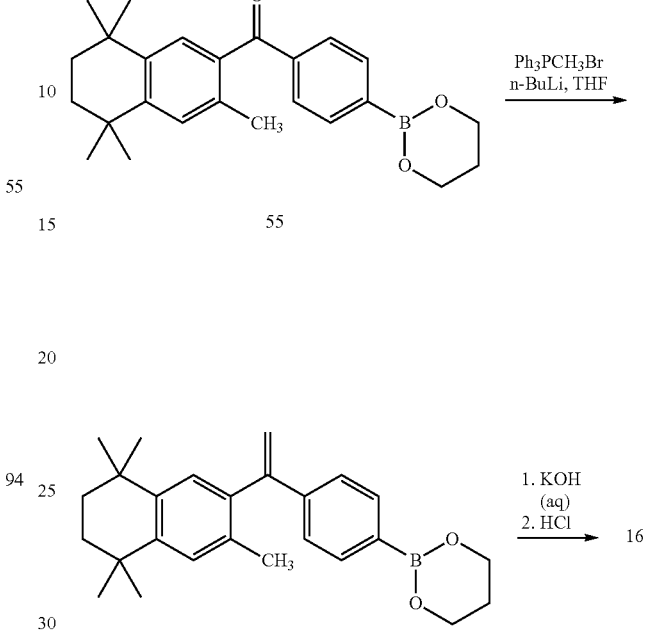

Analog 17 will be constructed with the acid chloride (97) derived from compound 94 and thionyl chloride. The acid chloride 97 should acylate compound 35 to give ketone (98) that will either be saponified to the ketone acid (99) or converted to the alkene ester (100) and thence saponified to give analog 17 (Scheme 16)

SCHEME 16

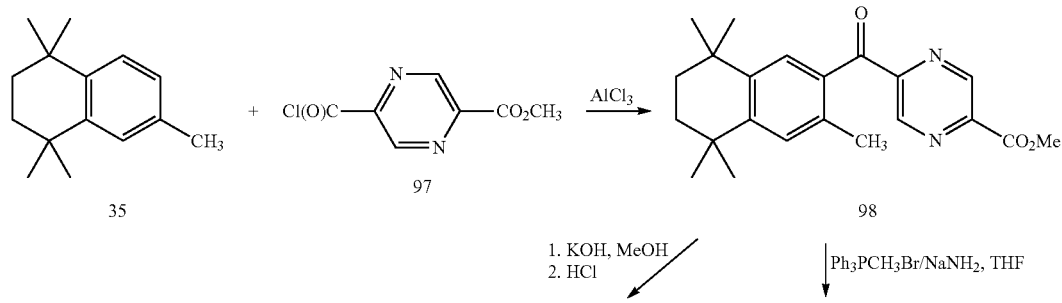

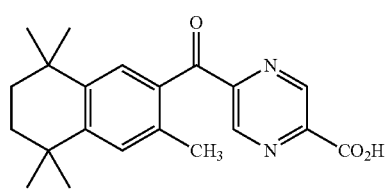

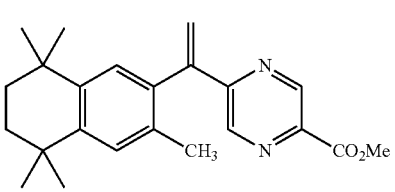

Analog 18, an unreported isomer of LG100268, is of interest to synthesize and test for binding and agonism of RXR, since the switch of the position of nitrogen in the aromatic ring may only slightly alter intermolecular interactions in the ligand binding domain (LBD) of RXR. The inventors expect analog 18 to be similarly potent to LG100268, however the difference in interactions between nonpolar residues in the RXR LBD, such as an absence of the 11e339 (isoleucine) side chain's proximal interaction with the nitrogen atom on LG10026855, may induce a slightly altered conformation of analog 18-bound RXR and modulate its interaction with other receptors.

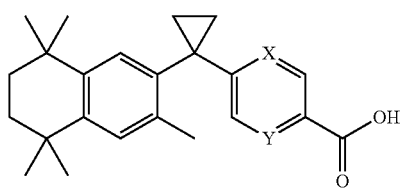

18 X = CH, Y = N
LG100268 X = N, Y = CH

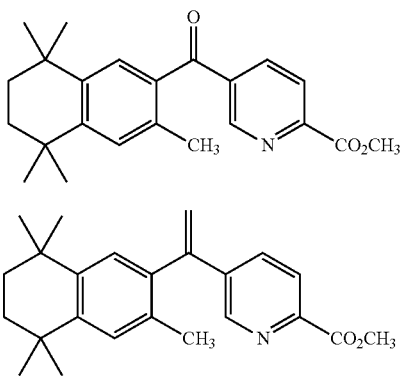

The synthesis of analog 18 is expected from alkene 101. Alkene 101 should be accessible from intermediate 61 through a Wittig reaction (Scheme 17).

SCHEME 17

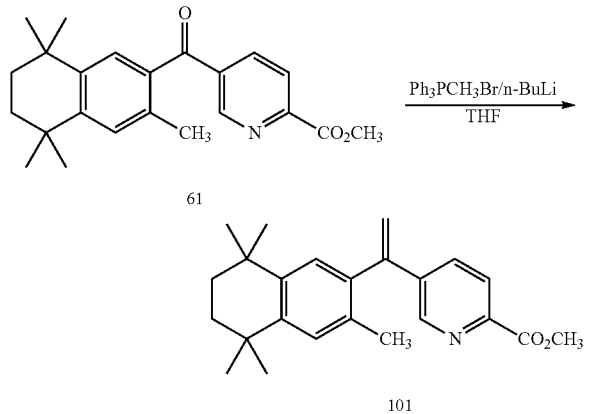

In the first published synthesis of LG100268, diethylzinc and chloroiodomethane were employed as the reagents for the critical cyclopropanation step, however, an alternative synthesis published later employed dimethylsulfoxonium methylide formed in situ from trimethylsufoxonium iodide to effect cyclopropanation. Thus, it is expected that the cyclopropanation of alkene 101 will give ester 102 that can be saponified to analog 18 (Scheme 18).

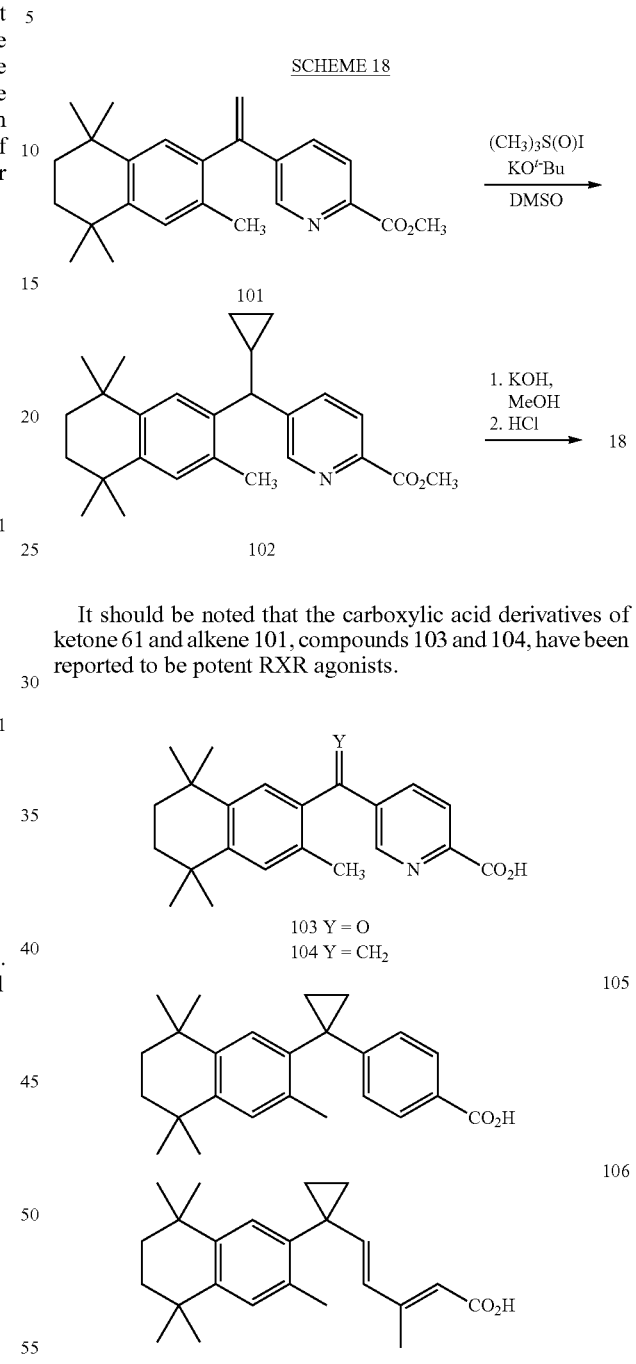

It should be noted that the carboxylic acid derivatives of ketone 61 and alkene 101, compounds 103 and 104, have been reported to be potent RXR agonists.

Interestingly, the reported crystal structure of LG100268 bound to hRXRβ led Love and co-workers to suggest that the tetrahedral nature of the quaternary cyclopropyl carbon in LG100268 helps to provide a bend that makes the LG100268 more specific to bind to RXR than a more flexible 9-cis-retinoic acid that can bind to both RXR and RAR.82 Corroborating this observation are the reports that both compounds 105 and 10683 are potent, RXR-selective agonists. It would be interesting to explore whether many of the alkene esters en route to analogs 4-17, in addition to 101, can form cyclopropane analogs as well.

There have been several reports of the successful application of molecular modeling to design selective RXR agonists, such as compounds 107 and 108 (UAB30), and one report that used modeling to explain the favor enantiomer (S)-109 of a racemic mixture of enantiomers 109(R,S) binding to the RXR ligand binding pocket.

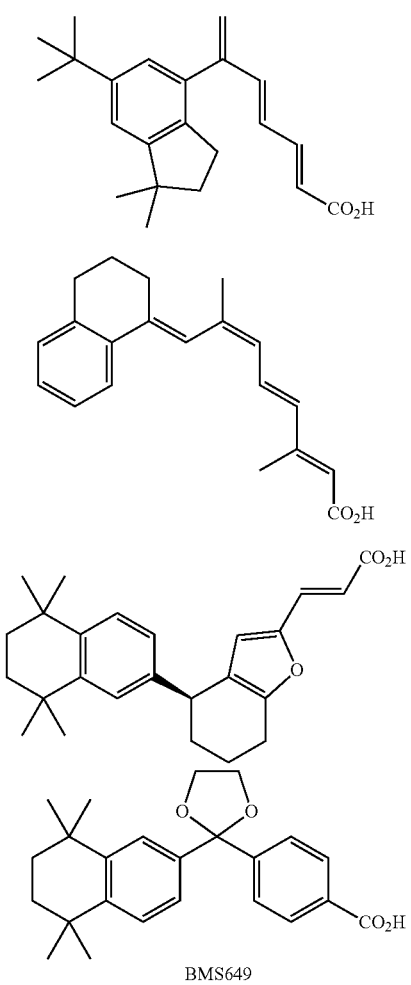

Most molecular modeling studies use the structure of the ligand binding pocket elucidated in the crystal structure of RXRα bound to its natural 9-cis RA ligand82, although other coordinates are available for hRXR bound to synthetic ligands such as LG10026855 or BMS64987 from the Worldwide Protein Data Bank (wwPDB).

Because molecular modeling is a key component of structure-based rational drug design, all of the proposed compounds of the invention, with the exception of 16 due to an absence of boronic acid modeling parameters, have been examined using the freely available AutoDock modeling program to test their binding affinity relative to bexarotene (FIG. 3).

Example 3

Biological Characterization

After compounds have been identified to bind in the mammalian two hybrid screen, and to transactivate in the RXRE-based assay, additional assays will be performed to determine the level of cytotoxicity induced by these agonists, their ability to induce apoptosis, and their mutagenicity. For example, the cytotoxicity will be assayed in the CTCL cells by performing a lactate dehydrogenase (LDH) assay (Cytotox 96® Non-Radioactive Cytotoxicity Assay, Promega). This assay colorimetrically determines the levels of LDH in the cell culture supernatant relative to controls. Intact cells do not leak cytosolic LDH into the cell culture supernatant, but damaged cells do. Thus the level of LDH in the cell culture supernatant is an established index of cell damage and cytotoxicity. LDH levels are indicated by a change in a tetrazolium salt into a red formazan compound, read by a microtiter plate reader.

Figure 5:
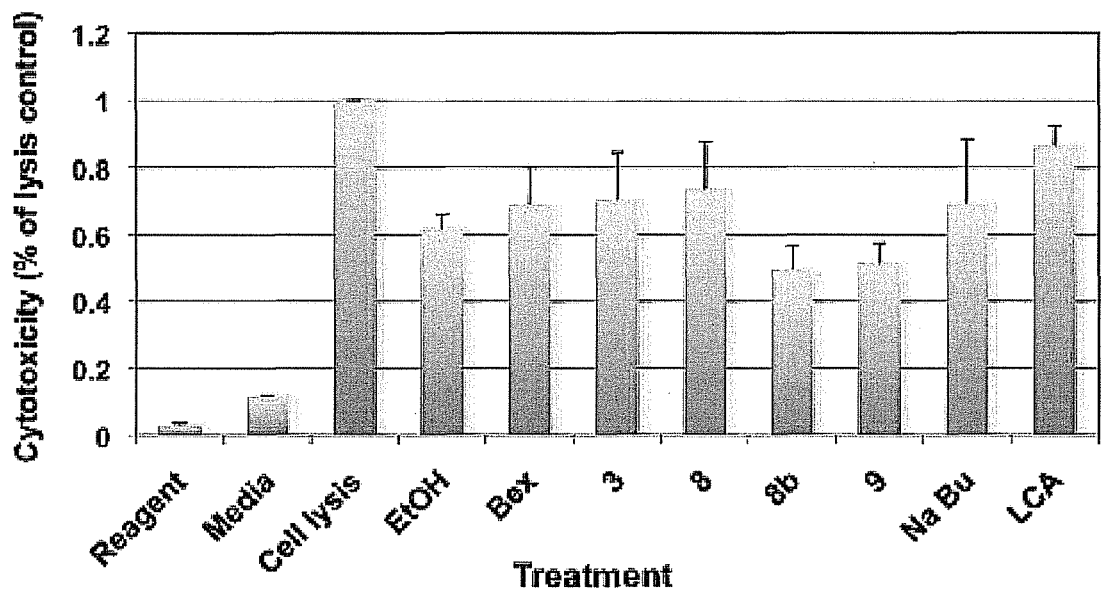
FIG. 5: Evaluation of bexarotene and selected analogs for cytotoxicity utilizing a lactate dehydrogenase-based assay in CTCL cells.

This assay has already been tested using some of the analogs described herein, and these cytotoxicity results for bexarotene and selected analogs are shown in FIG. 5. Some of the analogs that bind and activate RXR (compounds 3 and 8) also demonstrate promising cytotoxic activity similar to known cytotoxic agents such as sodium butyrate (NaBu) and lithocholic acid (LCA). Compound 8b, which displays little cytotoxic activity compared to the ethanol vehicle control, also does not bind RXR, suggesting the utility of this assay in the current screening protocol.

Figure 6:
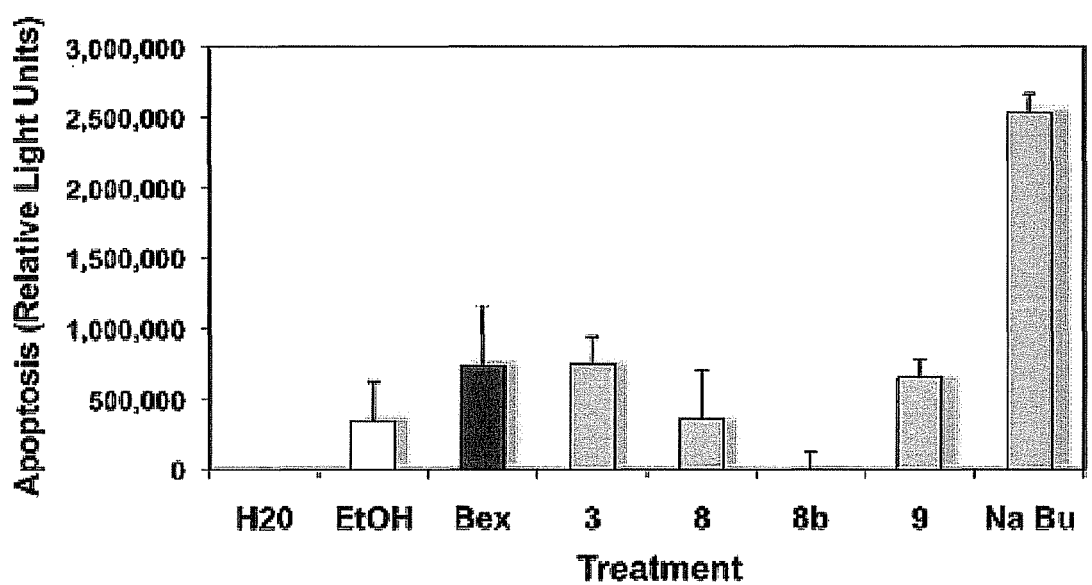
FIG. 6: Evaluation of bexarotene and selected analogs for apoptotic activity utilizing a Caspase 3/7 assay in CTCL cells.

It has been hypothesized that bexarotene treats CTCL effectively because it induces apoptosis and/or cytotoxicity in the T-lymphocyte cells. 94 Thus we will test CTCL cells treated with bexarotene and promising analogs for apoptosis, using the Promega Caspase Glo® 3/7 Assay. This assay determines intracellular activity of caspase 3 and 7 simultaneously. These two caspases are activated by upstream caspases and are considered "executioner caspases" by virtue of the fact that they destroy cell integrity during apoptosis. The reagent has substrates for each of these apoptosis-activated proteases, which is cleaved to a luminescent product, assayed in a luminometer. Once cells activate the apoptotic pathway, these proteases (and others) are activated and cell death eventually occurs. Nonapoptotic cells do not activate caspases, and do not demonstrate caspase activity in this assay. Some of the analogs of the invention have been analyzed analogs in this assay, and the results of bexarotene and selected analogs for apoptotic activity are summarized in FIG. 6. Some of the analogs that bind and activate RXR (compounds 3 and 9) also possess apoptotic activity similar to a known apoptotic inducer (NaBu). Compound 8b, which displays almost no apoptotic activity, also does not bind RXR, again suggesting the utility of this assay in the current screening protocol.

Determination of mutagenicity is important in order to decide if a compound should be pursued further for human therapeutic use. Potential human therapeutic compounds should be tested early on for DNA mutagenic properties, even before the compounds are testing in animals, to eliminate mutagenic compounds before more costly animal studies are performed. Compounds that possess apoptotic and/or cytotoxic activity will be tested in two assays to determine mutagenicity, the Ames test and an EPA approved *Saccharomyces cerevisiae* assay (described above) The Ames Test (also known as the *Salmonella* Mutagenicity Assay) is standard for determining mutagenic potential of pharmaceuticals. This test utilizes a series of *Salmonella typhimurium* strains, each of which cannot synthesize histidine because of a different mutation in a histidine biosynthetic gene. The strains are treated with the compound, and growth on plates lacking histidine is scored. The wild type *Salmonella* strains will not grow on the media, because they lack the ability to synthesize histidine. The strain will only grow if the compound indices a reverse mutation, indicating that the compound is a mutagen. Additionally, the compounds are treated with a rat liver microsomal fraction to simulate digestion and subsequent activity of the P450 enzymes in the liver; this mixture is also used in the Ames test to determine if P450 enzymes activate the compound from a harmless compound to a mutagenic one. This assay allows evaluation of a panel of *Salmonella* strains, each of which tests for one type of mutation, and will expand our confidence that our lead compounds are not mutagenic.

Finally, the RXR serves as a heterodimeric partner for a number of other nuclear receptors. Studies of the role of the RXR transcriptional activation function-2 (AF-2) domain in the context of RAR-RXR heterodimers have suggested that RAR silences RXR activity in the absence of an RAR ligand.16b Upon RAR ligand binding, an allosteric change in conformation allows the generation of an active RXR AF-2 that can putatively interact with transcriptional coactivators. Under these conditions, RXR can respond to its specific ligand and affect transcription through synergy with RAR ligands.

Previous studies have indicated that binding of 1,25(OH) 2D3 by VDR renders its RXR heterodimeric partner hyposensitve to the effects of its cognate ligand.16b This suggests that in the context of the VDR-RXR heterodimer, the contribution of the RXR AF-2 to the overall activity is dictated by the 1,25(OH)2D3 status of its VDR partner. Furthermore, addition of high concentrations of RXR ligand can divert the RXR protein away from the RXR-VDR heterodimer (and RXR-TR), and towards formation of RXR homodimers, resulting in potential and unwanted side-effects of therapeutic rexinoid compounds. However, it has been observed that on some VDREs, the RXR ligand results in a synergistic response in the presence of 1,25(OH)2D3. Under these circumstances, VDR and RXR may be employing a mechanism of AF-2 allosteric regulation similar to that observed with RAR-RXR. Therefore, we propose to evaluate those analogs with RXR binding activity (as assessed in the mammalian two-hybrid and RXRE-based assays) in a separate assay that employs a vitamin D responsive element (VDRE) linked to the luciferase reporter gene. This assay will allow us to evaluate if our novel analogs can either synergize or antagonize the actions of 1,25(OH)2D3 via the RXR-VDR heterodimer. In this system, human cells (Caco-2 and CTCL) will be transfected with the VDRE-luciferase construct and treated with 1,25(OH)2D3 alone and in combination with an active rexinoid. The activity of the luciferase reporter gene will reveal the presence of potential repressive or additive rexinoid effects towards VDR-1,25(OH)2D3-mediated transcriptional signaling. Because these effects may be both cell- and VDRE-dependent, we will utilize the 2 human cell lines listed above, as well as distinct VDRE reporter constructs, including the CYP24 VDREs, the CYP3A4 VDREs, and human p21 VDRE. A parallel approach will be employed using TRE- and RARE-based luciferase reporter constructs to investigate the ability of identified rexinoids to either potentiate or repress TR- and RAR-mediated transcription. This approach will allow one to distinguish novel RXR analogs that do not adversely affect other RXR requiring pathways and thus lead to undesired clinical side-effects.

Example 4

Regulation of Anti-Cancer Genes by Analogs of the Invention

The use of retinoids and rexinoids as potential cancer therapeutics is dependent on their ability to regulate gene networks that lead to repression of tumor associated genes while simultaneously inducing genes associated with chemoprotection, and at the same time minimizing the regulation of genes that can lead to undesirable clinical side-effects. The RXR agonists of the invention may be tested by treating human CTCL cells with the identified compounds followed by analysis of the set of genes that are regulated by our novel analogs using oligonucleotide microarray technology. This approach has already been used to successfully identify a number of growth regulation genes in human breast cells that respond to treatment with bexarotene. In fact, bexarotene-dosed cells will serve as a basis of comparison when evaluating our novel bexarotene analogs in gene chip experiments.

Genes identified by microarray studies will be validated through the use of RT-PCR. Indeed, genes already identified as major responders to bexarotene via upregulation (DEPP, KRT15, RTP801, LOXL2) or downregulation (COX-2, EGR3, ASNS, CTH) in breast tissue could be directly assayed by RT-PCR in the cell culture system. Cells treated with bexarotene and our analogs could be readily evaluated by RT-PCR of these key genes in an effort to quickly screen for those target genes that display a differential response to analog treatment versus bexarotene.

DNA microarray analysis is a method to assess genome-wide gene expression by simultaneously quantitating mRNA levels from all or a subset of genes in a genome and comparing these levels between a control and an experimental sample. These changes are compared, such as in as wild type versus mutant strains or cells with no treatment compared to cells treated with a reagent. RNA is extracted from the two cell types, and either converted to cDNA or amplified to cRNA, and then this message pool is used to assess gene expression changes. Both pools of labeled message are hybridized to a DNA microarray (or "gene chip"). These microarrays have all genes in the genome spotted onto the array in a precise fashion, such that this chip experiment becomes a genome-wide northern blot, assaying the message levels of all genes in the cells. Since the control and the experimental are hybridized to the same chip, there can be direct comparisons performed between the starting mRNA levels of the two, looking for genes that are under or over expressed in the experimental as compared to the control, analyzing the intensity of the hybridization of both cDNA pools.

The total RNA will be isolated from human CTCL cells, either untreated or treated with bexarotene or the appropriate analog. The RNA quality and integrity will be tested before hybridization using denaturing gel electrophoresis as well as reverse transcription followed by PCR. Once high quality RNA is isolated, labeled cRNA can be generated with the Genisphere 350 kit. Microarrays are readily available for such tests, for example, human microarrays can be obtained from Washington University St. Louis (Human HEEBO microarrays), or alternatively from the Toronto Microarray Centre (Toronto, Canada).

In order to demonstrate the feasibility of the microarray analysis, a microarray experiment was performed using CTCL cells. CTCL cells were treated bexarotene or ethanol vehicle control and total RNA was extracted after 4-hour treatment using the BioRad Aurum Total RNA Mini kit. Total RNA extracted was utilized to produce cRNA using a Genisphere 350 kit and was used to hybridize human HEEBO microarray slides obtained from GCAT (Genome Consortium for Active Teaching). The Genisphere 350 kit high sensitivity protocol was used and representative results were obtained (data not shown). Preliminary analysis of themicroarray indicates that there are several interesting candidate genes induced and repressed by bexarotene in CTCL cells. For example, several genes that could be involved in inhibiting tumorigenesis or inducing apoptosis are upregulated after treatment of bexarotene. Death associated protein kinase 3, a kinase activated in apoptosis, is upregulated 4.3-fold; urocortin, a protein that inhibits tumorigenesis, is upregulated 3.5- fold; and endothelin converting enzyme 1, a protein that has certain isoforms associated with favorable prognosis in neuroblastoma, is upregulated 4.6-fold. Likewise, there was a 2.9-fold downregulation of REEP, a gene that occurs in a deleted segment of human 5q31 in malignant myeloid diseases; and 2.6-fold downregulation of RAC GAP1, a GTPase activating protein of RAC, a protein required for malignant cell movement106; and 2.5-fold downregulation of karyopherin alpha 1 (importing alpha 5), a protein required for STAT1 import into the nucleus. Thus, it is demonstrated that a gene chip system can be used to test the analogs of the invention and compare them to bexarotene in terms of potential differential gene expression.

References

1. Dawson, M. I., Hobbs, P. D., La Vista-Picard, N., Pfahl, M., and M. Pfahl 1996. The receptor-DNA determines the retinoid response: a mechanism for the diversification of the ligand signal. *Molecular and Cellular Biology*. Vol. 16 (8), 4137-4146.
2. Fujii, H. et al. 1997. Metabolic inactivation of retinoic acid by a novel P450 differentially expressed in developing mouse embryos. *The EMBO Journal*. Vol. 16, 4163-4173.
3. Heller, E. H. & Shiffman, N. J. 1985. Synthetic retinoids in dermatology. *Canadian Medical Association Journal*. Vol. 132 (10), 1129-1136.
4. Prince, M. H., McCormack, C., Ryan, G., Baker, C., Rotstein, H., Davison, J., Yocum, R. 2001. *Australasian Journal of Dermatology*. Vol. 42 (2), 91-97.
5. Sporn, M. B. 1979. Retinoids and Cancer Prevention. *A Cancer Journal for Clinicians*. Vol. 29, 120-125.
6. Shibakura, M., Koyama, T., Saito, T., Shudo, K., Miyasaka, N., Kamiyama, R. and Shinsaku Hirosawa. 1997. *Blood*. Vol. 90 (4), 1545-1551.
7. Thomas, P. 2002. Retinoid Metabolism: a balancing act. *Nature Genetics*. Vol. 31, 7-8.
8. Vahlquist, A. 1999. What are Natural Retinoids? *Dermatology*. Vol. 199, 3-11
9. White, J. A. et al. 1996. Identification of the retinoic acid-inducible all-trans-retinoic acid 4-hydroxylase. *Journal of Biological Chemistry*. Vol. 271, 29922-29927.
10. Zimmermann, F. K. (1975). Procedures used in the induction of mitotic recombination and mutation in the yeast *Saccharomyces cerevisiae*. Mutat. Res. 31, 71-86.
11. Zimmermann, F. K., Kern, R., and Rasenberger, H. (1975). A yeast strain for simultaneous detection of mitotic crossing over, mitotic gene conversion, and reverse mutation. Mutat. Res. 28, 381-388.

The invention claimed is:

1. A compound having the structural formula:

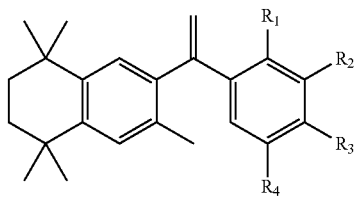

wherein $R_1$ is hydrogen, halogen, or $CO_2H$;
$R_2$ is halogen, or $CO_2H$;
$R_3$ is $CO_2H$; and
$R_4$ is hydrogen, halogen, or $CO_2H$; or a pharmaceutically acceptable salt thereof.

2. The compound or pharmaceutically acceptable salt of claim 1, wherein $R_1$ is a halogen.

3. The compound or pharmaceutically acceptable salt of claim 2, wherein $R_4$ is a halogen.
4. The compound or pharmaceutically acceptable salt of claim 3, wherein said halogen is selected from the group consisting of F, Br, Cl, and I, and said halogen is the same as the halogen at $R_1$ or different from the halogen at $R_1$.
5. The compound or pharmaceutically acceptable salt of claim 3, wherein $R_2$ is a halogen.
6. The compound or pharmaceutically acceptable salt of claim 5, wherein said halogen is selected from the group consisting of F, Br, Cl, and I, and said halogen is the same as the halogen at $R_1$ and/or $R_4$ or different from the halogen at $R_1$ and/or $R_4$.
7. The compound of claim 1 wherein $R_1$ is H, $R_2$ is F, $R_3$ is COOH, and $R_4$ is F.
8. A compound having the structural formula:

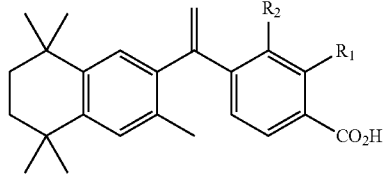

or a pharmaceutically acceptable salt thereof wherein $R_2$ and $R_1$ are defined as:

| Compound # | $R_1$ | $R_2$ |
|---|---|---|
| 10 | Cl | H |
| 11 | Br | H |
| 12 | I | H |
| 10a | H | Cl |
| 11a | H | Br |
| 12a | H | I |
| 10b | Cl | Cl |
| 11b | Br | Br |
| 12b | I | I. |

9. The compound of claim 1 which is a compound of formula:

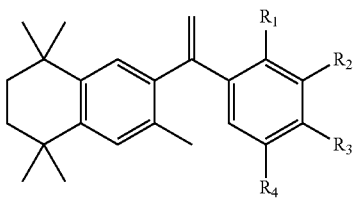

or a pharmaceutically acceptable salt thereof having the following substituents at each of positions $R_1$, $R_2$, $R_3$, $R_4$:

| Compound # | $R_1$ | $R_2$ | $R_3$ | $R_4$ |
|---|---|---|---|---|
| 4 | H | $CO_2H$ | $CO_2H$ | H |
| 5 | H | $CO_2H$ | $CO_2H$ | $CO_2H$ |
| 6 | F | F | $CO_2H$ | H |
| 7 | H | F | $CO_2H$ | F. |

10. A pharmaceutical composition comprising a compound or pharmaceutically acceptable salt of claim 1 and a pharmaceutically acceptable carrier.

* * * * *